US006887679B2

(12) United States Patent
Brown

(10) Patent No.: US 6,887,679 B2
(45) Date of Patent: *May 3, 2005

(54) METHODS FOR IDENTIFYING CONTRAINDICATIONS TO ANGIOTENSIN CONVERTING ENZYME INHIBITOR AND/OR VASOPEPTIDASE INHIBITOR TREATMENT

(75) Inventor: Nancy J. Brown, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 61 days.

This patent is subject to a terminal disclaimer.

(21) Appl. No.: 10/423,714

(22) Filed: Apr. 25, 2003

(65) Prior Publication Data

US 2003/0180828 A1 Sep. 25, 2003

Related U.S. Application Data

(62) Division of application No. 10/002,593, filed on Oct. 31, 2001, now Pat. No. 6,586,198.
(60) Provisional application No. 60/244,524, filed on Oct. 31, 2000.

(51) Int. Cl.$^7$ ............................................... C12Q 1/37
(52) U.S. Cl. .......................................... 435/24; 435/23
(58) Field of Search ........................... 435/24, 23, 212; 514/921

(56) References Cited

U.S. PATENT DOCUMENTS

| 4,314,936 | A |   | 2/1982 | Yaron et al. |
| 6,399,349 | B1 | * | 6/2002 | Ryan et al. ................. 435/226 |
| 6,586,198 | B2 | * | 7/2003 | Brown ........................ 435/23 |
| 6,610,497 | B1 | * | 8/2003 | Acton et al. ................. 435/7.1 |
| 2003/0083339 | A1 | * | 5/2003 | Tamura ................... 514/263.4 |

OTHER PUBLICATIONS

Asher J. Vasopeptidase Inhibition: A New Direction in Cardiovascular Treatment. Current Hypertension Reports 2(4)384–391, Aug. 2000.*

Ersahin C., "Inhibition of both Aminopeptidase P and ACE Prevents Bradykinin Degradation in the Rat Coronary Circulation", J. of Cardiovascular Pharmacology, 30(1):96–101 (1997).

Kim, K., "Inhibition of Aminopeptidase P Potentiates Wheal Response to Bradykinin in Ace Inhibitor Treated Human", J. of Pharmacology and Experimental Therapeutics, 292(1):295–298 (Jan. 2000).

Brown, N., "Recurrent ACE Inhibitor Associated Angioedema", JAMA 278(3)232–233 (Jul. 1997).

* cited by examiner

Primary Examiner—Ralph Gitomer
(74) Attorney, Agent, or Firm—Jenkins, Wilson & Taylor, P.A.

(57) ABSTRACT

Deficiencies in certain physiological pathways are linked with ACE or vasopeptidase inhibitor associated angioedema. Additionally, detection and/or measurement of dipeptidyl peptidase IV (DPP IV) enzyme activity and aminopeptidase P (APP) enzyme activity is a predictor of this risk. The present invention provides biological markers, diagnostic tests, and pharmaceutical indications that are useful in the diagnosis and treatment of angioedema and in the marketing and safety of certain medications. This ability can be important for the treatment of a subject that is in need of or are taking an angiotensin-converting enzyme (ACE) inhibitor and/or a vasopeptidase inhibitor (combined ACE and neutral endopeptidase (NEP) inhibitor), which are commonly used in the treatment of hypertension (high blood pressure), diabetes, and cardiac and renal diseases.

16 Claims, 4 Drawing Sheets

Catalysis of Ang I to Ang II by ACE

Enzymatic Pathways Acting on Bradykinin

Enzymatic Pathways Acting on Substance P

SEQUENCE LISTING

```
<160> NUMBER OF SEQ ID NOS: 10

<210> SEQ ID NO 1
<211> LENGTH: 10
<212> TYPE: PRT
<213> ORGANISM: Homo sapiens

<400> SEQUENCE: 1

Asp Arg Val Tyr Ile His Pro Phe His Leu
1               5                   10

<210> SEQ ID NO 2
<211> LENGTH: 8
<212> TYPE: PRT
<213> ORGANISM: Homo sapiens

<400> SEQUENCE: 2

Asp Arg Val Tyr Ile His Pro Phe
1               5

<210> SEQ ID NO 3
<211> LENGTH: 9
<212> TYPE: PRT
<213> ORGANISM: Homo sapiens

<400> SEQUENCE: 3

Arg Pro Pro Gly Phe Ser Pro Phe Arg
1               5

<210> SEQ ID NO 4
<211> LENGTH: 11
<212> TYPE: PRT
<213> ORGANISM: Homo sapiens

<400> SEQUENCE: 4

Arg Pro Lys Pro Gln Gln Phe Phe Gly Leu Met
1               5                   10

<210> SEQ ID NO 5
<211> LENGTH: 3407
<212> TYPE: DNA
<213> ORGANISM: Homo sapiens

<400> SEQUENCE: 5
cgcgcgtctc cgccgcccgc gtgacttctg cctgcgctcc ttctctgaac gctcacttcc      60
gaggagacgc cgacgatgaa gacaccgtgg aagattcttc tgggactgct gggtgctgct     120
gcgcttgtca ccatcatcac cgtgcccgtg gttctgctga acaaaggcac agatgatgct     180
acagctgaca gtcgcaaaac ttacactcta actgattact aaaaaatac  ttatagactg     240 aagttatact ccttaagatg gatttcagat catgaatatc tctacaaaca agaaaataat     300
atcttggtat tcaatgctga atatggaaac agctcagttt tcttggagaa cagtacattt     360
gatgagtttg gacattctat caatgattat tcaatatctc ctgatgggca gtttattctc     420
ttagaataca actacgtgaa gcaatggagg cattcctaca gcttcata tgacatttat     480 gatttaaata aaaggcagct gattacagaa gagaggattc caaacaacac acagtgggtc     540
```

```
acatggtcac cagtgggtca taaattggca tatgtttgga acaatgacat ttatgttaaa    600
attgaaccaa atttaccaag ttacagaatc acatggacgg ggaaagaaga tataatatat    660
aatgaataa  ctgactgggt ttatgaagag gaagtcttca gtgcctactc tgctctgtgg    720
tggtctccaa acggcacttt tttagcatat gcccaattta acgacacaga agtcccactt    780
attgaatact ccttctactc tgatgagtca ctgcagtacc caaagactgt acgggttcca    840
tatccaaagg caggagctgt gaatccaact gtaaagttct tgttgtaaa  tacagactct    900
ctcagctcag tcaccaatgc aacttccata caaatcactg ctcctgcttc tatgttgata    960
ggggatcact acttgtgtga tgtgacatgg gcaacacaag aaagaatttc tttgcagtgg   1020
ctcaggagga ttcagaacta ttcggtcatg gatatttgtg actatgatga atccagtgga   1080
agatggaact gcttagtggc acggcaacac attgaaatga gtactactgg ctgggttgga   1140
agatttaggc cttcagaacc tcattttacc cttgatggta atagcttcta caagatcatc   1200
agcaatgaag aaggttacag acacatttgc tatttccaaa tagataaaaa agactgcaca   1260
tttattacaa aaggcacctg ggaagtcatc gggatagaag ctctaaccag tgattatcta   1320
tactacatta gtaatgaata taaggaatg  ccaggaggaa ggaatcttta taaaatccaa   1380
cttattgact atacaaaagt gacatgcctc agttgtgagc tgaatccgga aaggtgtcag   1440
tactattctg tgtcattcag taaagaggcg aagtattatc agctgagatg ttccggtcct   1500
ggtctgcccc tctatactct acacagcagc gtgaatgata aagggctgag agtcctggaa   1560
gacaattcag ctttggataa aatgctgcag aatgtccaga tgccctccaa aaaactggac   1620
ttcattattt tgaatgaaac aaaattttgg tatcagatga tcttgcctcc tcattttgat   1680
aaatccaaga aatatcctct actattagat gtgtatgcag gcccatgtag tcaaaaagca   1740
gacactgtct tcagactgaa ctgggccact taccttgcaa gcacagaaaa cattatagta   1800
gctagctttg atgcagagg  aagtggttac caaggagata agatcatgca tgcaatcaac   1860
agaagactgg gaacatttga agttgaagat caaattgaag cagccagaca attttcaaaa   1920
atgggatttg tggacaacaa acgaattgca atttggggct ggtcatatgg agggtacgta   1980
acctcaatgg tcctgggatc gggaagtggc gtgttcaagt gtggaatagc cgtggcgcct   2040
gtatcccggt gggagtacta tgactcagtg tacacagaac gttacatggg tctcccaact   2100
ccagaagaca accttgacca ttacagaaat tcaacagtca tgagcagagc tgaaaatttt   2160
aaacaagtta gtacctcct  tattcatgga acagcagatg ataacgttca ctttcagcag   2220
tcagctcaga tctccaaagc cctggtcgat gttggagtgg atttccaggc aatgtggtat   2280
actgatgaag accatggaat agctagcagc acagcacacc aacatatata tacccacatg   2340
agccacttca taaaacaatg tttctcttta ccttagcacc tcaaaatacc atgccattta   2400
agcttatta  aaactcattt ttgttttcat tatctcaaaa ctgcactgtc aagatgatga   2460
tgatctttaa aatacacact caaatcaaga aacttaaggt tacctttgtt cccaaatttc   2520
atacctatca tcttaagtag ggacttctgt cttcacaaca gattattacc ttacagaagt   2580
ttgaattatc cggtcgggtt ttattgttta aaatcatttc tgcatcagct gctgaaacaa   2640
caaataggaa ttgttttat  ggaggctttg catagattcc ctgagcagga ttttaatctt   2700
tttctaactg gactggttca aatgttgttc tcttctttaa agggatggca agatgtgggc   2760
agtgatgtca ctagggcagg gacaggataa gagggattag ggagagaaga tagcagggca   2820
tggctgggaa cccaagtcca agcataccaa cacgagcagg ctactgtcag ctcccctcgg   2880
```

-continued

```
agaagagctg ttcaccacga gactggcaca gttttctgag aaagactatt caaacagtct    2940
caggaaatca aatatcgaaa gcactgactt ctaagtaaac cacagcagtt gaaagactcc    3000
aaagaaatgt aagggaaact gccagcaacg cagcccccag gtgccagtta tggctatagg    3060
tgctacaaaa acacagcaag ggtgatggga aagcattgta aatgtgcttt taaaaaaaaa    3120
tactgatgtt cctagtgaaa gaggcagctt gaaactgaga tgtgaacaca tcagcttgcc    3180
ctgttaaaag atgaaaatat ttgtatcaca aatcttaact tgaaggagtc cttgcatcaa    3240
tttttcttat ttcatttctt tgagtgtctt aattaaaaga atattttaac ttccttggac    3300
tcattttaaa aaatggaaca taaaatacaa tgttatgtat tattattccc attctacata    3360
ctatggaatt tctcccagtc atttaataaa tgtgccttca ttttttc                  3407
```

<210> SEQ ID NO 6
<211> LENGTH: 766
<212> TYPE: PRT
<213> ORGANISM: Homo sapiens

<400> SEQUENCE: 6

```
Met Lys Thr Pro Trp Lys Ile Leu Leu Gly Leu Leu Ala Ala Ala
 1               5                  10                  15

Leu Val Thr Ile Ile Thr Val Pro Val Val Leu Leu Asn Lys Gly Thr
                20                  25                  30

Asp Asp Ala Thr Ala Asp Ser Arg Lys Thr Tyr Thr Leu Thr Asp Tyr
                35                  40                  45

Leu Lys Asn Thr Tyr Arg Leu Lys Leu Tyr Ser Leu Arg Trp Ile Ser
 50                  55                  60

Asp His Glu Tyr Leu Tyr Lys Gln Glu Asn Asn Ile Leu Val Phe Asn
 65                  70                  75                  80

Ala Glu Tyr Gly Asn Ser Ser Val Phe Leu Glu Asn Ser Thr Phe Asp
                85                  90                  95

Glu Phe Gly His Ser Ile Asn Asp Tyr Ser Ile Ser Pro Asp Gly Gln
                100                 105                 110

Phe Ile Leu Leu Glu Tyr Asn Tyr Val Lys Gln Trp Arg His Ser Tyr
                115                 120                 125

Thr Ala Ser Tyr Asp Ile Tyr Asp Leu Asn Lys Arg Gln Leu Ile Thr
                130                 135                 140

Glu Glu Arg Ile Pro Asn Asn Thr Gln Trp Val Thr Trp Ser Pro Val
145                 150                 155                 160

Gly His Lys Leu Ala Tyr Val Trp Asn Asn Asp Ile Tyr Val Lys Ile
                165                 170                 175

Glu Pro Asn Leu Pro Ser Tyr Arg Ile Thr Trp Thr Gly Lys Glu Asp
                180                 185                 190

Ile Ile Tyr Asn Gly Ile Thr Asp Trp Val Tyr Glu Glu Val Phe
                195                 200                 205

Ser Ala Tyr Ser Ala Leu Trp Trp Ser Pro Asn Gly Thr Phe Leu Ala
                210                 215                 220

Tyr Ala Gln Phe Asn Asp Thr Glu Val Pro Leu Ile Glu Tyr Ser Phe
225                 230                 235                 240

Tyr Ser Asp Glu Ser Leu Gln Tyr Pro Lys Thr Val Arg Val Pro Tyr
                245                 250                 255

Pro Lys Ala Gly Ala Val Asn Pro Thr Val Lys Phe Phe Val Val Asn
                260                 265                 270

Thr Asp Ser Leu Ser Ser Val Thr Asn Ala Thr Ser Ile Gln Ile Thr
                275                 280                 285
```

-continued

```
Ala Pro Ala Ser Met Leu Ile Gly Asp His Tyr Leu Cys Asp Val Thr
    290                 295                 300
Trp Ala Thr Gln Glu Arg Ile Ser Leu Gln Trp Leu Arg Arg Ile Gln
305                 310                 315                 320
Asn Tyr Ser Val Met Asp Ile Cys Asp Tyr Asp Glu Ser Ser Gly Arg
                325                 330                 335
Trp Asn Cys Leu Val Ala Arg Gln His Ile Glu Met Ser Thr Thr Gly
            340                 345                 350
Trp Val Gly Arg Phe Arg Pro Ser Glu Pro His Phe Thr Leu Asp Gly
        355                 360                 365
Asn Ser Phe Tyr Lys Ile Ile Ser Asn Glu Glu Gly Tyr Arg His Ile
    370                 375                 380
Cys Tyr Phe Gln Ile Asp Lys Lys Asp Cys Thr Phe Ile Thr Lys Gly
385                 390                 395                 400
Thr Trp Glu Val Ile Gly Ile Glu Ala Leu Thr Ser Asp Tyr Leu Tyr
                405                 410                 415
Tyr Ile Ser Asn Glu Tyr Lys Gly Met Pro Gly Gly Arg Asn Leu Tyr
            420                 425                 430
Lys Ile Gln Leu Ile Asp Tyr Thr Lys Val Thr Cys Leu Ser Cys Glu
        435                 440                 445
Leu Asn Pro Glu Arg Cys Gln Tyr Tyr Ser Val Ser Phe Ser Lys Glu
    450                 455                 460
Ala Lys Tyr Tyr Gln Leu Arg Cys Ser Gly Pro Gly Leu Pro Leu Tyr
465                 470                 475                 480
Thr Leu His Ser Ser Val Asn Asp Lys Gly Leu Arg Val Leu Glu Asp
                485                 490                 495
Asn Ser Ala Leu Asp Lys Met Leu Gln Asn Val Gln Met Pro Ser Lys
            500                 505                 510
Lys Leu Asp Phe Ile Ile Leu Asn Glu Thr Lys Phe Trp Tyr Gln Met
        515                 520                 525
Ile Leu Pro Pro His Phe Asp Lys Ser Lys Lys Tyr Pro Leu Leu Leu
    530                 535                 540
Asp Val Tyr Ala Gly Pro Cys Ser Gln Lys Ala Asp Thr Val Phe Arg
545                 550                 555                 560
Leu Asn Trp Ala Thr Tyr Leu Ala Ser Thr Glu Asn Ile Ile Val Ala
                565                 570                 575
Ser Phe Asp Gly Arg Gly Ser Gly Tyr Gln Gly Asp Lys Ile Met His
            580                 585                 590
Ala Ile Asn Arg Arg Leu Gly Thr Phe Glu Val Glu Asp Gln Ile Glu
        595                 600                 605
Ala Ala Arg Gln Phe Ser Lys Met Gly Phe Val Asp Asn Lys Arg Ile
    610                 615                 620
Ala Ile Trp Gly Trp Ser Tyr Gly Gly Tyr Val Thr Ser Met Val Leu
625                 630                 635                 640
Gly Ser Gly Ser Gly Val Phe Lys Cys Gly Ile Ala Val Ala Pro Val
                645                 650                 655
Ser Arg Trp Glu Tyr Tyr Asp Ser Val Tyr Thr Glu Arg Tyr Met Gly
            660                 665                 670
Leu Pro Thr Pro Glu Asp Asn Leu Asp His Tyr Arg Asn Ser Thr Val
        675                 680                 685
Met Ser Arg Ala Glu Asn Phe Lys Gln Val Glu Tyr Leu Leu Ile His
    690                 695                 700
```

-continued

| Gly | Thr | Ala | Asp | Asp | Asn | Val | His | Phe | Gln | Gln | Ser | Ala | Gln | Ile | Ser |
|-----|-----|-----|-----|-----|-----|-----|-----|-----|-----|-----|-----|-----|-----|-----|-----|
| 705 |     |     |     |     | 710 |     |     |     |     | 715 |     |     |     |     | 720 |

| Lys | Ala | Leu | Val | Asp | Val | Gly | Val | Asp | Phe | Gln | Ala | Met | Trp | Tyr | Thr |
|-----|-----|-----|-----|-----|-----|-----|-----|-----|-----|-----|-----|-----|-----|-----|-----|
|     |     |     |     | 725 |     |     |     |     | 730 |     |     |     |     | 735 |     |

| Asp | Glu | Asp | His | Gly | Ile | Ala | Ser | Ser | Thr | Ala | His | Gln | His | Ile | Tyr |
|-----|-----|-----|-----|-----|-----|-----|-----|-----|-----|-----|-----|-----|-----|-----|-----|
|     |     |     | 740 |     |     |     |     | 745 |     |     |     |     | 750 |     |     |

| Thr | His | Met | Ser | His | Phe | Ile | Lys | Gln | Cys | Phe | Ser | Leu | Pro |
|-----|-----|-----|-----|-----|-----|-----|-----|-----|-----|-----|-----|-----|-----|
|     |     |     | 755 |     |     |     |     | 760 |     |     |     |     | 765 |

<210> SEQ ID NO 7
<211> LENGTH: 2366
<212> TYPE: DNA
<213> ORGANISM: Homo sapiens
<220> FEATURE:
<221> NAME/KEY: misc_feature
<222> LOCATION: (1)..(2366)
<223> OTHER INFORMATION: n is any nucleotide

<400> SEQUENCE: 7

```
gcgnccgctc ccacttcaga ttgaacctaa cgaggtgaca cactcaggag acacaggtgt      60
ggaaacagac ggcagaatgc ctccaaaggt gacttcagag ctgcttcggc agctgagaca     120
agccatgagg aactctgagt atgtgaccga accgatccag gcctacatca tcccatcggg     180
agatgctcat cagagtgagt atattgctcc atgtgactgt cggcgggctt ttgtctctgg     240
attcgatggc tctgcgggca cagccatcat cacagaagag catgcagcca tgtggactga     300
cgggcgctac tttctccagg ctgccaagca aatggacagc aactggacac ttatgaagat     360
gggtctgaag gacacaccaa ctcaggaaga ctggctggtg agtgtgcttc ctgaaggatc     420
cagggttggt gtggacccct tgatcattcc tacagattat tggaagaaaa tggccaaagt     480
tctgagaagt gccggccatc acctcattcc tgtcaaggag aacctcgttg acaaaatctg     540
gacagaccgt cctgagcgcc cttgcaagcc tctcctcaca ctgggcctgg attacacagg     600
catctcctgg aaggacaagg ttgcagacct tcggttgaaa atggctgaga ggaacgtcat     660
gtggtttgtg gtcactgcct tggatgagat tgcgtggcta tttaatctcc gaggatcaga     720
tgtggagcac aatccagtat ttttctccta cgcaatcata ggactagaga cgatcatgct     780
cttcattgat ggtgaccgca tagacgcccc cagtgtgaag gagcacctgc ttcttgactt     840
gggtctggaa gccgaataca ggatccaggt gcatccctac aagtccatcc tgagcgagct     900
caaggccctg tgtgctgacc tctccccaag ggagaaggtg tgggtcagtg acaaggccag     960
ctatgctgtg agcgagacca tcccaaggac ccaccgctgc tgtatgcctt acacccccat    1020
ctgcatcgcc aaagctgtga agaattcagc tgagtcagaa ggcatgaggc cggctcacat    1080
taaagatgct gttgctctct gtgaactctt taactggctg gagaaagagg ttcccaaagg    1140
tggtgtgaca gagatctcag ctgctgacaa agctgaggag tttcgcaggc aacaggcaga    1200
cttttgtgga ctgagcttcc caacaatttc cagtacggga cccaacggcg ccatcattca    1260
ctacgcgcca gtccctgaga cgaataggac cttgtccctg gatgaggtgt accttattga    1320
ctcgggtgct caatacaagg atggcaccac agatgtgacg cggacaatgc attttgggac    1380
ccctacagcc tacgagaagg aatgcttcac atatgtcctc aagggccaca tagctgtgag    1440
tgcagccgtt ttcccgactg aaccaaaggt caccttcttg actcctttg cccgttcagc    1500
tttatgggat tcaggcctag attacttgca cgggactgga catggtgttg gtcttttttt    1560
gaatgtccat gagggtcctt gcggcatcag ttacaaaaca ttctctgatg agcccttgga    1620
ggcaggcatg attgtcactg atgagcccgg gtactatgaa gatgggcttt tggaattcg     1680
```

-continued

```
cattgagaat gttgtccttg tggttcctgt gaagaccaag tataatttta ataaccgggg    1740
aagcctgacc tttgaacctc taacattggt tccaattcag accaaaatga tagatgtgga    1800
ttctcttaca gacaaagagt gcgactggct caacaattac cacctgacct gcagggatgt    1860
gattgggaag gaattgcaga acagggccg ccaggaagct ctcgagtggc tcatcagaga     1920
gacgcaaccc atctccaaac agcattaata aatacctccc cggttttgtt tttgtaaaat    1980
gctctggagg aaggaagaaa cgtggcagat ccctgacatc tttcccctt ccttccttc      2040 ttccctacct ccccttttta ctttagactt taagaagaac agaaaatctt cttatcctct    2100
ttgatatttt attgcaaaca ctcagtcttt tatgatttt taattgttga gaacaagcca     2160
agaataaaat tgctgcacca gaaggagggt ccctccaaag ttgaacactt ggtgaaagga    2220
agatgccccg acttctttgg ccagtgatgg ggaatcagtg agtgctccat gatggtcatg    2280
ttccaggtgc tagtacatca ttcatgatca ccttaatgct catgagacta tatttatgat    2340
cagtgaataa aaatgtcaga actgtg                                        2366
```

<210> SEQ ID NO 8
<211> LENGTH: 623
<212> TYPE: PRT
<213> ORGANISM: Homo sapiens

<400> SEQUENCE: 8

```
Met Pro Pro Lys Val Thr Ser Glu Leu Leu Arg Gln Leu Arg Gln Ala
1               5                   10                  15

Met Arg Asn Ser Glu Tyr Val Thr Glu Pro Ile Gln Ala Tyr Ile Ile
                20                  25                  30

Pro Ser Gly Asp Ala His Gln Ser Glu Tyr Ile Ala Pro Cys Asp Cys
            35                  40                  45

Arg Arg Ala Phe Val Ser Gly Phe Asp Gly Ser Ala Gly Thr Ala Ile
        50                  55                  60

Ile Thr Glu Glu His Ala Ala Met Trp Thr Asp Gly Arg Tyr Phe Leu
65                  70                  75                  80

Gln Ala Ala Lys Gln Met Asp Ser Asn Trp Thr Leu Met Lys Met Gly
                85                  90                  95

Leu Lys Asp Thr Pro Thr Gln Glu Asp Trp Leu Val Ser Val Leu Pro
            100                 105                 110

Glu Gly Ser Arg Val Gly Val Asp Pro Leu Ile Ile Pro Thr Asp Tyr
        115                 120                 125

Trp Lys Lys Met Ala Lys Val Leu Arg Ser Ala Gly His His Leu Ile
    130                 135                 140

Pro Val Lys Glu Asn Leu Val Asp Lys Ile Trp Thr Asp Arg Pro Glu
145                 150                 155                 160

Arg Pro Cys Lys Pro Leu Leu Thr Leu Gly Leu Asp Tyr Thr Gly Ile
                165                 170                 175

Ser Trp Lys Asp Lys Val Ala Asp Leu Arg Leu Lys Met Ala Glu Arg
            180                 185                 190

Asn Val Met Trp Phe Val Val Thr Ala Leu Asp Glu Ile Ala Trp Leu
        195                 200                 205

Phe Asn Leu Arg Gly Ser Asp Val Glu His Asn Pro Val Phe Phe Ser
    210                 215                 220

Tyr Ala Ile Ile Gly Leu Glu Thr Ile Met Leu Phe Ile Asp Gly Asp
225                 230                 235                 240

Arg Ile Asp Ala Pro Ser Val Lys Glu His Leu Leu Leu Asp Leu Gly
```

-continued

```
                    245                 250                 255
Leu Glu Ala Glu Tyr Arg Ile Gln Val His Pro Tyr Lys Ser Ile Leu
                260                 265                 270

Ser Glu Leu Lys Ala Leu Cys Ala Asp Leu Ser Pro Arg Glu Lys Val
            275                 280                 285

Trp Val Ser Asp Lys Ala Ser Tyr Ala Val Ser Glu Thr Ile Pro Lys
        290                 295                 300

Asp His Arg Cys Cys Met Pro Tyr Thr Pro Ile Cys Ile Ala Lys Ala
305                 310                 315                 320

Val Lys Asn Ser Ala Glu Ser Glu Gly Met Arg Pro Ala His Ile Lys
                325                 330                 335

Asp Ala Val Ala Leu Cys Glu Leu Phe Asn Trp Leu Glu Lys Glu Val
                340                 345                 350

Pro Lys Gly Gly Val Thr Glu Ile Ser Ala Ala Asp Lys Ala Glu Glu
            355                 360                 365

Phe Arg Arg Gln Gln Ala Asp Phe Val Asp Leu Ser Phe Pro Thr Ile
        370                 375                 380

Ser Ser Thr Gly Pro Asn Gly Ala Ile Ile His Tyr Ala Pro Val Pro
385                 390                 395                 400

Glu Thr Asn Arg Thr Leu Ser Leu Asp Glu Val Tyr Leu Ile Asp Ser
                405                 410                 415

Gly Ala Gln Tyr Lys Asp Gly Thr Thr Asp Val Thr Arg Thr Met His
                420                 425                 430

Phe Gly Thr Pro Thr Ala Tyr Glu Lys Glu Cys Phe Thr Tyr Val Leu
            435                 440                 445

Lys Gly His Ile Ala Val Ser Ala Ala Val Phe Pro Thr Gly Thr Lys
        450                 455                 460

Gly His Leu Leu Asp Ser Phe Ala Arg Ser Ala Leu Trp Asp Ser Gly
465                 470                 475                 480

Leu Asp Tyr Leu His Gly Thr Gly His Gly Val Gly Ser Phe Leu Asn
                485                 490                 495

Val His Glu Gly Pro Cys Gly Ile Ser Tyr Lys Thr Phe Ser Asp Glu
            500                 505                 510

Pro Leu Glu Ala Gly Met Ile Val Thr Asp Glu Pro Gly Tyr Tyr Glu
        515                 520                 525

Asp Gly Ala Phe Gly Ile Arg Ile Glu Asn Val Val Leu Val Val Pro
    530                 535                 540

Val Lys Thr Lys Tyr Asn Phe Asn Asn Arg Gly Ser Leu Thr Phe Glu
545                 550                 555                 560

Pro Leu Thr Leu Val Pro Ile Gln Thr Lys Met Ile Asp Val Asp Ser
                565                 570                 575

Leu Thr Asp Lys Glu Cys Asp Trp Leu Asn Asn Tyr His Leu Thr Cys
                580                 585                 590

Arg Asp Val Ile Gly Lys Glu Leu Gln Lys Gln Gly Arg Gln Glu Ala
            595                 600                 605

Leu Glu Trp Leu Ile Arg Glu Thr Gln Pro Ile Ser Lys Gln His
        610                 615                 620
```

<210> SEQ ID NO 9
<211> LENGTH: 3428
<212> TYPE: DNA
<213> ORGANISM: Homo sapiens

<400> SEQUENCE: 9

-continued

| | | | | |
|---|---|---|---|---|
| caccctatcc | tacactacta | ggaacttgca | cagtccgcct | cgggcagccc | aaagctcctc | 60 |
| tgcccaccct | ggctcccaaa | accctccaaa | acaaaagacc | agaaaagcac | tctccaccca | 120 |
| gcagccaaac | gcctccttct | tgacgccagc | ccccaccctc | tgtctgctcg | agcccaggaa | 180 |
| aggcctgaag | gaacaggccg | ggaaggagc | cctccctctc | tcccttgtcc | ctccatccac | 240 |
| ccagcgccgg | catctggaga | ccctatggcc | cgggctcact | gggctgctg | cccctggctg | 300 |
| gtcctcctct | gtgcttgtgc | ctgggccac | acaaagccac | tggaccttgg | agggcaggat | 360 |
| gtgagaaatt | gttccaccaa | ccccccttac | cttccagtta | ctgtggtcaa | taccacaatg | 420 |
| tcactcacag | ccctccgcca | gcagatgcag | acccagaatc | tctcagccta | catcatccca | 480 |
| ggcacagatg | ctcacatgaa | cgagtacatc | ggccaacatg | acgagaggcg | tgcgtggatt | 540 |
| acaggcttta | cagggtctgc | aggaactgca | gtggtgacta | tgaagaaagc | agctgtctgg | 600 |
| accgacagtc | gctactggac | tcaggctgag | cggcaaatgg | actgtaattg | ggagctccat | 660 |
| aaggaagttg | gcaccactcc | tattgtcacc | tggctcctca | ccgagattcc | cgctggaggg | 720 |
| cgtgtgggtt | ttgacccctt | cctcttgtcc | attgacacct | gggagagtta | tgatctggcc | 780 |
| ctccaaggct | ctaacagaca | gctggtgtcc | atcacaacca | atcttgtgga | cctggtatgg | 840 |
| ggatcagaga | ggccaccggt | tccaaatcaa | cccatttatg | ccctgcagga | ggcattcaca | 900 |
| gggagcactt | gcaggagaa | agtatctggc | gtccgaagcc | agatgcagaa | gcatcaaaag | 960 |
| gtcccgactg | ccgtccttct | gtcggcgctt | gaggagacgg | cctggctctt | caaccttcga | 1020 |
| gccagtgaca | tccctataa | ccccttcttc | tattcctaca | cgctgctcac | agactcttct | 1080 |
| attaggttgt | ttgcaaacaa | gagtcgcttt | agctccgaaa | ccttgagcta | tctgaactcc | 1140 |
| agttgcacag | gccccatgtg | tgtgcaaatc | gaggattaca | gccaagttcg | tgacagcatc | 1200 |
| caggcctact | cattgggaga | tgtgaggatc | tggattggga | ccagctatac | catgtatggg | 1260 |
| atctatgaaa | tgataccaag | ggagaaactc | gtgacagaca | cctactcccc | agtgatgatg | 1320 |
| accaaggcag | tgaagaacag | caaggagcag | gccctcctca | aggccagcca | cgtgcgggac | 1380 |
| gctgtggctg | tgatccggta | cttggtctgg | ctggagaaga | acgtgcccaa | aggcacagtg | 1440 |
| gatgagtttt | cggggcaga | gatcgtggac | aagttccgag | gagaagaaca | gttctcctcc | 1500 |
| ggacccagtt | ttgaaaccat | ctctgctagt | ggtttgaatg | ctgccctggc | ccactacagc | 1560 |
| ccgaccaagg | agctgaaccg | caagctgtcc | tcagatgaga | tgtacctgct | ggactctggg | 1620 |
| gggcagtact | gggacgggac | cacagacatc | accagaacag | tccactgggg | cacccccctct | 1680 |
| gcctttcaga | aggaggcata | tacccgtgtg | ctgataggaa | atattgacct | gtccaggctc | 1740 |
| atctttcccg | ctgctacatc | agggcgaatg | gtggaggcct | ttgcccgcag | agccttgtgg | 1800 |
| gatgctggtc | tcaattatgg | tcatgggaca | ggccacggca | ttggcaactt | cctgtgtgtg | 1860 |
| catgagtggc | cagtgggatt | ccagtccaac | aacatcgcta | tggccaaggg | catgttcact | 1920 |
| tccattgaac | ctggttacta | taaggatgga | gaatttggga | tccgtctcga | agatgtggct | 1980 |
| ctcgtggtag | aagcaaagac | caagtaccca | ggggagctac | ctgaccttgt | ggtatcattt | 2040 |
| gtgcccttatg | accggaacct | catcgatgtc | agcctgctgt | ctcccgagca | tctccagtac | 2100 |
| ctgaatcgct | actaccagac | catccgggag | aaggtgggtc | cagagctgca | gaggcgccag | 2160 |
| ctactagagg | agttcgagtg | gcttcaacag | cacacagagc | cctggccgc | cagggcccca | 2220 |
| gacaccgcct | cctgggcctc | tgtgttagtg | gtctccaccc | ttgccatcct | ggctggagt | 2280 |
| gtctagaggc | tccagactct | cctgttaacc | ctccatctag | atgggggct | cccttgctta | 2340 |
| gctccccctca | ccctgcactg | aacatacccc | aagagcccct | gctggcccat | tgcctagaaa | 2400 |

-continued

```
cctttgcatt catcctcctt ctccaagacc tatggagaag gtcccaggcc ccaggaaaca    2460
cagggcttct tggccccaga tggcacctcc ctgcaccccg gggttgtata ccacaccctg    2520
ggcccctaat cccaggcccc gaaataggaa agccagctag tctcttctct tctgtgatct    2580
cagtaggcct aacctataac ctaacacaga ctgctacagc tgctcccctc ccgccaaaca    2640 aagcccccaag aaaacaatgc ccctaccacc caagggtgcc atggtcccgg gaaacccaa    2700 cctgtcaccg cgtgttgggc gtaaccagaa ctgttccccc ccaccagggc ttaaaaatcg    2760
cccccacttt ttaaccatcg tccattaacc acctggtggg catagccaga gctgttcgaa    2820
cccagccagg gatgaaaaat caaccccccga catggaaccc atgattccta aacccggggt    2880
aggttccatg ccaagtaaca gcagagggag ttaagccata ggaatttggc tgtggagtaa    2940
gagggaatgc ggtgaggcag tgtggaatat gaccctacca gaggttggag aacaaacttg    3000
ggcagccgga acccgtcact attttagatt cctggcattc gaggagccct ttgaactttc    3060
caaagtgcag ccacagctac aatgctgtta atcctccca catttcttgg atgccccttc    3120
accttgtgtg gacagtgtct ggtttcccca ttttacagac aggaaaactg agcttcagac    3180
agggggtggg ctttgcctaa ggacacacaa atttggttgg gagttgatgg ggccagatga    3240
gccagcattc cagctgtttc acccttcagc aacatgcaga gtccctgagc ccacctccca    3300
gccctctcct cattctctga acccactgtg gtgagaagaa tttgctccgg ccaaattggc    3360
cgttagccac ctgggtccac atcctgctaa gacgtttaaa acagcctaac aaagacactt    3420
gcctgtgg                                                              3428
```

<210> SEQ ID NO 10
<211> LENGTH: 493
<212> TYPE: PRT
<213> ORGANISM: Homo sapiens

<400> SEQUENCE: 10

```
Val Ser Ile Thr Thr Asn Leu Val Asp Leu Val Trp Gly Ser Glu Arg
1               5                   10                  15

Pro Pro Val Pro Asn Gln Pro Ile Tyr Ala Leu Gln Glu Ala Phe Thr
            20                  25                  30

Gly Ser Thr Trp Gln Glu Lys Val Ser Gly Val Arg Ser Gln Met Gln
        35                  40                  45

Lys His Gln Lys Val Pro Thr Ala Val Leu Leu Ser Ala Leu Glu Glu
    50                  55                  60

Thr Ala Trp Leu Phe Asn Leu Arg Ala Ser Asp Ile Pro Tyr Asn Pro
65                  70                  75                  80

Phe Phe Tyr Ser Tyr Thr Leu Leu Thr Asp Ser Ser Ile Arg Leu Phe
                85                  90                  95

Ala Asn Lys Ser Arg Phe Ser Ser Glu Thr Leu Ser Tyr Leu Asn Ser
            100                 105                 110

Ser Cys Thr Gly Pro Met Cys Val Gln Ile Glu Asp Tyr Ser Gln Val
        115                 120                 125

Arg Asp Ser Ile Gln Ala Tyr Ser Leu Gly Asp Val Arg Ile Trp Ile
    130                 135                 140

Gly Thr Ser Tyr Thr Met Tyr Gly Ile Tyr Glu Met Ile Pro Arg Glu
145                 150                 155                 160

Lys Leu Val Thr Asp Thr Tyr Ser Pro Val Met Met Thr Lys Ala Val
                165                 170                 175

Lys Asn Ser Lys Glu Gln Ala Leu Leu Lys Ala Ser His Val Arg Asp
```

-continued

```
              180                 185                 190
Ala Val Ala Val Ile Arg Tyr Leu Val Trp Leu Glu Lys Asn Val Pro
            195                 200                 205
Lys Gly Thr Val Asp Glu Phe Ser Gly Ala Glu Ile Val Asp Lys Phe
            210                 215                 220
Arg Gly Glu Glu Gln Phe Ser Ser Gly Pro Ser Phe Glu Thr Ile Ser
225                 230                 235                 240
Ala Ser Gly Leu Asn Ala Ala Leu Ala His Tyr Ser Pro Thr Lys Glu
                245                 250                 255
Leu Asn Arg Lys Leu Ser Ser Asp Glu Met Tyr Leu Leu Asp Ser Gly
            260                 265                 270
Gly Gln Tyr Trp Asp Gly Thr Thr Asp Ile Thr Arg Thr Val His Trp
            275                 280                 285
Gly Thr Pro Ser Ala Phe Gln Lys Glu Ala Tyr Thr Arg Val Leu Ile
            290                 295                 300
Gly Asn Ile Asp Leu Ser Arg Leu Ile Phe Pro Ala Ala Thr Ser Gly
305                 310                 315                 320
Arg Met Val Glu Ala Phe Ala Arg Arg Ala Leu Trp Asp Ala Gly Leu
                325                 330                 335
Asn Tyr Gly His Gly Thr Gly His Gly Ile Gly Asn Phe Leu Cys Val
                340                 345                 350
His Glu Trp Pro Val Gly Phe Gln Ser Asn Asn Ile Ala Met Ala Lys
            355                 360                 365
Gly Met Phe Thr Ser Ile Glu Pro Gly Tyr Tyr Lys Asp Gly Glu Phe
            370                 375                 380
Gly Ile Arg Leu Glu Asp Val Ala Leu Val Val Glu Ala Lys Thr Lys
385                 390                 395                 400
Tyr Pro Gly Glu Leu Pro Asp Leu Val Val Ser Phe Val Pro Tyr Asp
                405                 410                 415
Arg Asn Leu Ile Asp Val Ser Leu Leu Ser Pro Glu His Leu Gln Tyr
                420                 425                 430
Leu Asn Arg Tyr Tyr Gln Thr Ile Arg Glu Lys Val Gly Pro Glu Leu
            435                 440                 445
Gln Arg Arg Gln Leu Leu Glu Glu Phe Glu Trp Leu Gln Gln His Thr
            450                 455                 460
Glu Pro Leu Ala Ala Arg Ala Pro Asp Thr Ala Ser Trp Ala Ser Val
465                 470                 475                 480
Leu Val Val Ser Thr Leu Ala Ile Leu Gly Trp Ser Val
                485                 490
```

METHODS FOR IDENTIFYING CONTRAINDICATIONS TO ANGIOTENSIN CONVERTING ENZYME INHIBITOR AND/ OR VASOPEPTIDASE INHIBITOR TREATMENT

CROSS REFERENCE TO RELATED APPLICATIONS

The present application is a divisional of U.S. patent application Ser. No. 10/002,593, filed Oct. 31, 2001, now U.S. Pat. No. 6,586,198, which is based on and claims priority to U.S. Provisional Application Ser. No. 60/244,524, entitled "Biological Markers and Diagnostic Tests for Angiotensin Converting Enzyme Inhibitor and Vasopeptidase Inhibitor Associated Angioedema", which was filed Oct. 31, 2000, each of which is incorporated herein by reference.

GRANT STATEMENT

This invention was made with federal grant money under NIH grants HL56963, GM 07569 and 5M01 RR-00095. Thus, the United States Government has certain rights in the present invention.

TECHNICAL FIELD

The present invention relates generally to screening tests to determine which patients are at risk for developing angioedema associated with inhibitors of angiotensin converting enzyme (ACE) and/or combined ACE and neutral endopeptidase (NEP) inhibitors (a combined ACE/NEP inhibitor is referred to herein as a "vasopeptidase inhibitor"). More particularly, the present invention relates to an association between dipeptidyl peptidase IV (DPP IV) and aminopeptidase P (APP) enzymatic activity and ACE and vasopeptidase inhibitor-related angioedema. The present invention also provides screening tests and kits to identify a subject who is at risk for ACE and vasopeptidase inhibitor-associated angioedema.

| Abbreviations | |
|---|---|
| ACE | angiotensin converting enzyme |
| ACEI | angiotensin converting enzyme inhibitor |
| AGT | angiotensinogen |
| ANP | atrial natriutetic peptide |
| APP | aminopeptidase P |
| DPP IV | dipeptidyl peptidase IV |
| HTN | hypertensive |
| NCBI | National Center for Biotechnology Information |
| NEP | neutral endopeptidase |
| NLM | National Library of Medicine |
| NTN | normotensive |
| OMIM | Online Mendelian Inheritance in Man |
| RAS | renin-angiotensin system |

BACKGROUND ART

Administration of angiotensin-converting enzyme (ACE) inhibitors is common medical practice for the treatment of a variety of disease conditions, including: cardiac and renal diseases, diabetes, and hypertension (high blood pressure). Several combined ACE and neutral endopeptidase (NEP) inhibitors are presently under investigation or are awaiting regulatory approval for the treatment of the aforementioned disease conditions. However, the administration of an ACE and/or a vasopeptidase inhibitor (referred to herein as an ACE/vasopeptidase inhibitor) is contraindicated for subjects with a history of angioedema due to the potential severity of this side effect, which can be so severe as to result in death. Approximately 0.1% to 1.0% of the population receiving an ACE inhibitor is predicted to be susceptible to developing at least one episode of angioedema during treatment. This percentage might be even higher, especially for subjects taking a vasopeptidase inhibitor. Also, these inhibitors are often administered over long periods of time because the illnesses that they treat are often chronic conditions. This could increase the chances of a subject developing angioedema over a course of treatment.

Angioedema is an uncommon, but serious, side effect of ACE and vasopeptidase inhibitors. Currently, it is not possible to accurately predict which subjects are at risk to develop angioedema when taking an ACE or vasopeptidase inhibitor; however it is known that approximately 0.1% to 1.0% or more of the subjects receiving an ACE or vasopeptidase inhibitor will develop angioedema as a side effect. The variation in susceptibility to vasopeptidase-associated angioedema depends, in part, on the subgroup of the population that is analyzed. For example, African Americans are particularly susceptible to ACE inhibitor associated angioedema.

In patients who develop angioedema while taking one of these medications, it is difficult to determine if the angioedemic condition arose in response to the medication or due to some other occurrence. For example, certain allergic reactions can result in angioedema. The current standard in practice is to employ a treatment other than an ACE/vasopeptidase inhibitor, if a patient has a known history of angioedema, or to halt treatment with ACE/vasopeptidase inhibitors if a patient presents with symptoms of angioedema or it is learned after-the-fact that the patient has a history of angioedema. Most practitioners, however, consider these alternative therapies to be less effective in treating the original condition than ACE/vasopeptidase inhibitor therapy.

What is needed, therefore, are tests, assays, and biological markers for identifying patients that are at increased risk for developing angioedema related to treatment with ACE/vasopeptidase inhibitors, as compared to the general population or a matched population. Such assays would allow the continued use of ACE/vasopeptidase inhibitors in subjects that have a reduced susceptibility to angioedema and the rational regulation of their use in susceptible subjects. The present invention solves these and other problems, in part by providing biological markers and diagnostic tests and kits that are preferably employed early on in treatment, thereby averting complications.

SUMMARY OF THE INVENTION

A method of identifying a subject that is susceptible to developing an angioedemic condition during a course of treatment comprising administering one of an ACE inhibitor and a vasopeptidase inhibitor is disclosed. In a preferred embodiment, the method comprises (a) providing a biological sample obtained from a subject; (b) determining a dipeptidyl peptidase IV activity in the biological sample; and (c) comparing a dipeptidyl peptidase IV activity in the biological sample to a standard dipeptidyl peptidase IV activity, wherein a 10% or more reduction in the sample activity compared to the standard indicates that the subject is susceptible to developing an angioedema during a course of treatment comprising administering one of an ACE inhibitor and a vasopeptidase inhibitor. Preferably, the vasopeptidase inhibitor is an angiotensin-converting enzyme inhibitor or a neutral endopeptidase inhibitor. It is also preferable that a 20% or more reduction in the sample activity compared to the standard indicates that the subject is susceptible and that the subject is a human.

A method of identifying a subject that is susceptible to developing an angioedemic condition during a course of treatment comprising administering one of an ACE inhibitor and a vasopeptidase inhibitor is disclosed. In a preferred embodiment, the method comprises: (a) providing a biological sample obtained from a subject; (b) determining an aminopeptidase P activity in the biological sample; and (c) comparing an aminopeptidase P activity in the biological sample to a standard aminopeptidase P activity, wherein a 10% or more reduction in the sample activity compared to the standard indicates that the subject is susceptible to developing an angioedema during a course of treatment comprising administering one of an ACE inhibitor and a vasopeptidase inhibitor. Preferably, the vasopeptidase inhibitor is an angiotensin-converting enzyme inhibitor or a neutral endopeptidase inhibitor. It is also preferable that a 20% or more reduction in the sample activity compared to the standard indicates that the subject is susceptible and that the subject is a human.

A method of determining contraindication for administration of one of an ACE inhibitor and a vasopeptidase inhibitor to an individual is disclosed. In a preferred embodiment, the method comprises: (a) providing a biological sample obtained from a subject; (b) determining a dipeptidyl peptidase IV activity in the biological sample; and (c) comparing a dipeptidyl peptidase IV activity in the biological sample to a standard dipeptidyl peptidase IV activity, wherein administration of the vasopeptidase inhibitor is contraindicated when the dipeptidyl peptidase IV activity in the biological sample is outside the standard dipeptidyl peptidase IV activity range.

A method of determining contraindication for administration of one of an ACE inhibitor and a vasopeptidase inhibitor to an individual is disclosed. In a preferred embodiment, the method comprises: (a) providing a biological sample obtained from a subject; (b) determining an aminopeptidase P activity in the biological sample; and (c) comparing an aminopeptidase P activity in the biological sample to a standard aminopeptidase P activity, wherein administration of the vasopeptidase inhibitor is contraindicated when the aminopeptidase P activity in the biological sample is outside the standard aminopeptidase P activity range.

A method of screening an individual for compatibility with an administration of one of an ACE inhibitor and a vasopeptidase inhibitor is disclosed. In a preferred embodiment, the method comprises: (a) providing a biological sample obtained from a subject; (b) determining a dipeptidyl peptidase IV activity in the biological sample; and (c) comparing a dipeptidyl peptidase IV activity in the biological sample to a standard dipeptidyl peptidase IV activity range, wherein administration of the vasopeptidase inhibitor is contraindicated when the sample activity is outside the standard dipeptidyl peptidase IV activity range, and wherein administration of the vasopeptidase inhibitor is indicated when the sample activity is either within or above the standard dipeptidyl peptidase IV activity range. Preferably, the vasopeptidase inhibitor is an angiotensin-converting enzyme inhibitor or a neutral endopeptidase inhibitor.

A method of screening an individual for compatibility with an administration of one of an ACE inhibitor and a vasopeptidase inhibitor is disclosed. In a preferred embodiment, the method comprises (a) providing a biological sample obtained from a subject; (b) determining an aminopeptidase P activity in the biological sample; and (c) comparing an aminopeptidase P activity in the biological sample to a standard aminopeptidase P activity range, wherein administration of a vasopeptidase inhibitor is contraindicated when the sample activity is below the standard aminopeptidase P activity range, and wherein administration of the vasopeptidase inhibitor is indicated when the sample activity is either equal to or above the standard aminopeptidase P activity range. Preferably, the vasopeptidase inhibitor is an angiotensin-converting enzyme inhibitor or a neutral endopeptidase inhibitor.

A kit for identifying a subject at risk for angioedema during a course of treatment comprising administering one of an ACE inhibitor and a vasopeptidase inhibitor is disclosed. In a preferred embodiment, the kit comprises: (a) a substrate of a dipeptidyl peptidase IV enzyme; (b) a buffer; (c) a reaction stop solution; and (d) a set of instructions comprising information on a standard dipeptidyl peptidase IV activity range. Preferably, the article of manufacture further comprises a calibration solution for calibration of the reaction and the substrate is Gly-Pro-p-nitroanilide.

A kit for identifying a subject at risk for angioedema during a course of treatment comprising administering one of an ACE inhibitor and a vasopeptidase inhibitor is disclosed. In a preferred embodiment, the kit comprises: (a) an aminopeptidase P enzyme substrate; (b) a dilution buffer; (c) a reaction stop solution; (d) a revelation buffer; and (e) a set of instructions comprising information on a standard aminopeptidase P activity range. Preferably, the article of manufacture further comprises a calibration solution for calibration of the reaction and the substrate is the peptide Arg-Pro-Pro.

A kit for identifying a subject at risk for angioedema during a course of treatment comprising administering one of an ACE inhibitor and a vasopeptidase inhibitor is disclosed. In a preferred embodiment, the kit comprises (a) a vasopeptidase inhibitor; and (b) a packaging material comprising information that the vasopeptidase inhibitor is contraindicated for individuals with a serum dipeptidyl peptidase IV enzyme activity outside a standard dipeptidyl peptidase IV activity range.

A kit for identifying a subject at risk for angioedema during a course of treatment comprising administering one of an ACE inhibitor and a vasopeptidase inhibitor is disclosed. In a preferred embodiment, the kit comprises (a) a vasopeptidase inhibitor; and (b) a packaging material comprising information that the vasopeptidase inhibitor is contraindicated for individuals with a serum aminopeptidase P enzyme activity outside a standard aminopeptidase P activity range.

Another kit is disclosed and in a preferred embodiment comprises a vasopeptidase inhibitor and a packaging material, wherein the packaging material includes information that the vasopeptidase inhibitor is contraindicated for individuals with a dipeptidyl peptidase IV enzyme activity below a normal range or is indicated for individuals with a dipeptidyl peptidase IV enzyme activity within a normal range.

Another kit is disclosed and in a preferred embodiment comprises a vasopeptidase inhibitor and a packaging material, wherein the packaging material includes information that the vasopeptidase inhibitor is contraindicated for individuals with an aminopeptidase P enzyme activity below a normal range or is indicated for individuals with an aminopeptidase P enzyme activity within a normal range.

A method of marketing a vasopeptidase inhibitor is disclosed and in a preferred embodiment, the method comprises providing information about a diagnostic test adapted to identify a subject that is susceptible to angioedema as a result of taking the vasopeptidase inhibitor during a course of treatment comprising administering one of an ACE inhibitor and a vasopeptidase inhibitor. Preferably, the vasopeptidase inhibitor is an angiotensin-converting enzyme inhibitor, the diagnostic test comprises detecting an activity of a dipeptidyl peptidase IV enzyme or an aminopeptidase P enzyme in a biological sample from the subject, and the subject is a human. It is also preferable that the vasopeptidase inhibitor is a neutral endopeptidase inhibitor that the diagnostic test includes detecting an activity of a dipeptidyl peptidase IV enzyme or an aminopeptidase P enzyme in a biological sample from the subject, and the subject is a human.

Accordingly, it is an object of the present invention to provide a novel method and article for identifying a subject that is susceptible to developing an angioedemic condition during a course of treatment comprising administering one of an ACE inhibitor and a vasopeptidase inhibitor. This and other objects are achieved in whole or in part by the present invention.

An object of the invention having been stated hereinabove, other objects will be evident as the description proceeds, when taken in connection with the accompanying Drawings and Laboratory Examples as best described hereinbelow.

BRIEF DESCRIPTION OF THE SEQUENCES IN THE SEQUENCE LISTING

Figure 1:
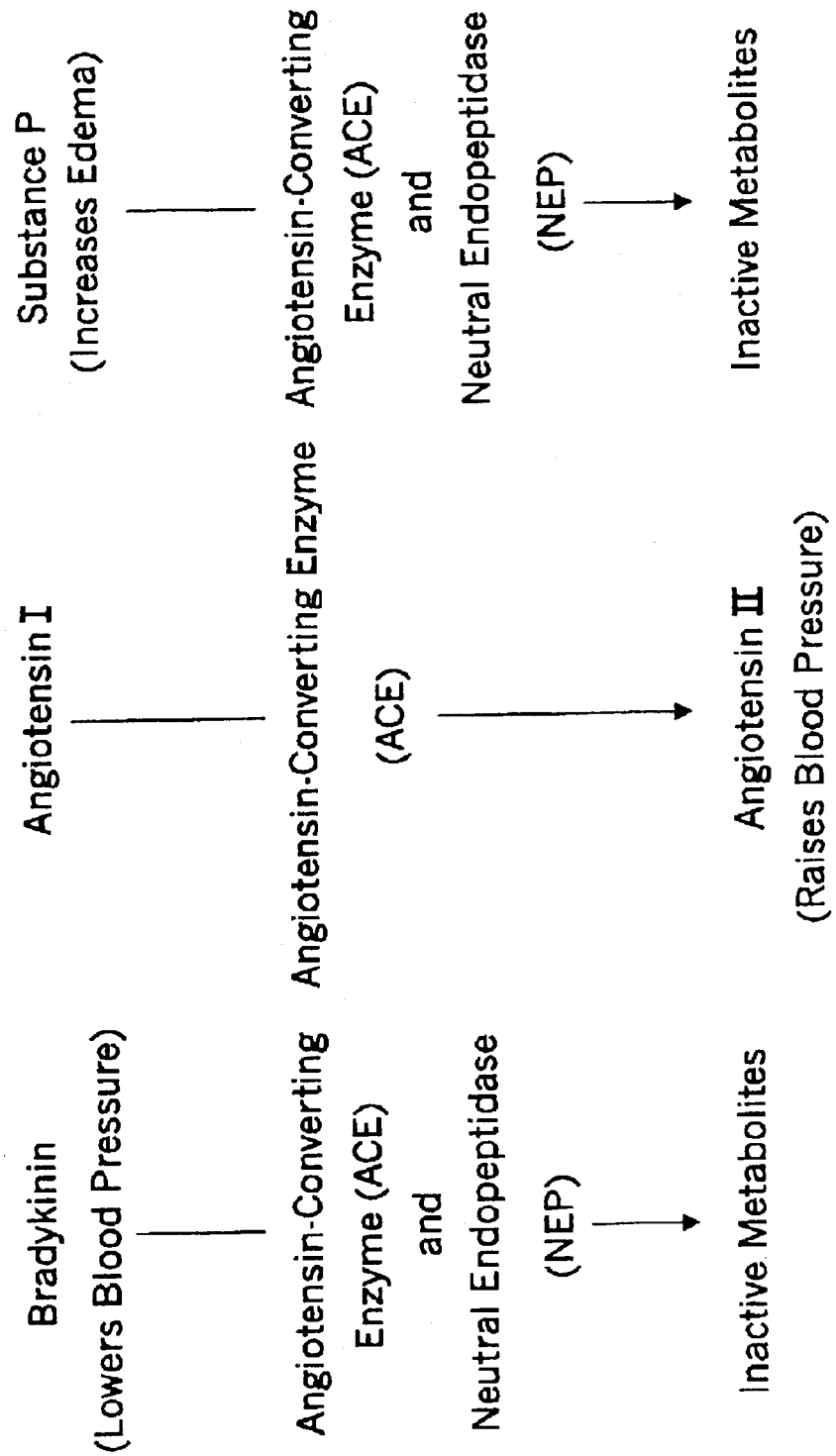
FIG. 1 is a diagram depicting an overview of selected portions of the renin-angiotensin system (RAS) and a Substance P metabolic pathway.

SEQ ID NO: 1 is an amino acid sequence of a peptide fragment of angiotensin I.

SEQ ID NO: 2 is an amino acid sequence of a peptide fragment of angiotensin II.

SEQ ID NO: 3 is an amino acid sequence of a peptide fragment of bradykin.

SEQ ID NO: 4 is an amino acid sequence of a peptide fragment of substance P.

SEQ ID NO: 5 is a nucleotide sequence encoding human dipeptidyl peptidase IV.

SEQ ID NO: 6 is an amino acid sequence of human dipeptidyl peptidase IV.

SEQ ID NO: 7 is a nucleotide sequence encoding a soluble form of human aminopeptidase P.

SEQ ID NO: 8 is an amino acid sequence of a soluble form of human aminopeptidase P.

SEQ ID NO: 9 is a nucleotide sequence encoding a membrane-bound form of human amino peptidase P.

SEQ ID NO: 10 is an amino acid sequence of a membrane-bound form of human amino peptidase P.

DETAILED DESCRIPTION OF THE INVENTION

The present invention provides biological markers, diagnostic tests, clinical assays, and articles of manufacture (such as kits useful in the tests and assays) for identifying an increased risk for developing ACE/vasopeptidase inhibitor-associated angioedema in a subject. The present invention also provides information for an appropriate course of treatment for individuals taking ACE/vasopeptidase inhibitor medications. The articles and methods of the present invention can also be employed to identify a subject that has a reduced risk for developing ACE/vasopeptidase inhibitor associated angioedema.

For example, by employing the articles of manufacture and methods of the present invention, a physician can determine whether or not treatment with an ACE/vasopeptidase inhibitor is advisable based upon a risk that the subject might develop angioedema. Likewise, a physician caring for a subject that has been started on an ACE/vasopeptidase inhibitor can learn that the subject has a history of one or more events of angioedema unrelated to ACE or vasopeptidase inhibitor treatment. The physician can employ the methods of the present invention to determine if the subject is susceptible to ACE/vasopeptidase associated angioedema. If not, or if the risk is low, then the physician can continue treatment with the ACE/vasopeptidase inhibitor. If the subject is determined to be susceptible to developing ACE/vasopeptidase inhibitor angioedema, the physician can discontinue treatment with the ACE/vasopeptidase inhibitor, or can optionally select an alternative mode of treatment.

In another situation, a subject might present with angioedema while being treated with an ACE/vasopeptidase inhibitor. In this case, the physician typically would discontinue treatment with the ACE/vasopeptidase inhibitor until the angioedemic condition is resolved. The methods and articles of the present invention can be employed to determine whether the angioedema resulted from the administration of the ACE/vasopeptidase inhibitor or if it is likely to be due to another cause, whether defined or undefined. If the determination by the present invention is that the cause is not due to administration of the ACE/vasopeptidase inhibitor, then the physician can restart treatment with an ACE/vasopeptidase inhibitor. If the determination by the present invention is that the cause is due to administration of the ACE/vasopeptidase inhibitor (or likely due), then the physician can select an alternative mode of treatment (ACE/vasopeptidase inhibitors are contraindicated in this latter situation).

In another example, during the research, development, and/or manufacture of an ACE/vasopeptidase inhibitor compounds, a pharmaceutical company or other entity can employ the methods and articles of the present invention to evaluate the safety of the compounds. Alternatively, the entity might desire to screen test populations in order to identify subjects that are at increased risk of developing serious side effects, such as angioedema, associated with the administration of the compound(s) being tested. This can make the testing period more safe for the subjects being evaluated. Moreover, the present invention can reduce the possibility of negative consequences from the sale of ACE/vasopeptidase inhibitors because, after a assessment performed with the methods and articles of the present invention, the ACE/vasopeptidase inhibitors can be contraindicated for the populations that are most at risk.

In addition to the market for treatment of humans, ACE and/or vasopeptidase inhibitors are used to treat similar illness in pets, livestock and show animals and the methods and compositions of the present invention are generally applicable to these other mammals. The occurrence of angioedema as a side effect, even in a relatively small fraction of the population being treated with ACE/vasopeptidase inhibitors, has serious consequences in the marketability of these drugs and the availability of these drugs to the approximately 99% of the treated population that does not develop angioedema.

Animals so treated can be warm-blooded vertebrates, for instance, mammals and birds. More particularly, the animal can be selected from the group consisting of rodent, swine, bird, ruminant, and primate. Even more particularly, the animal can be selected from the group consisting of a mouse, a rat, a pig, a guinea pig, poultry, an emu, an ostrich, a goat, a cow, a sheep, and a rabbit. Most particularly, the animal can be a primate, such as an ape, a monkey, a lemur, a tarsier, a marmoset, or a human.

Thus, provided is the treatment of mammals such as humans, as well as those mammals of importance due to being endangered (such as Siberian tigers), of economical importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), and horses. Also provided is the treatment of birds, including the treatment of those kinds of birds that are endangered, kept in zoos, as well as fowl, and more particularly domesticated fowl, e.g., poultry, such as turkeys, chickens, ducks, geese, guinea fowl, and the like, as they are also of economical importance to humans. Thus, provided is the treatment of livestock, including, but not limited to, domesticated swine (pigs and hogs), ruminants, horses, poultry, and the like.

I. Definitions

Following long-standing patent law convention, the terms "a" and "an" mean "one or more" when used in this application, including the claims.

The term "about", as used herein when referring to a measurable value such as an amount of activity, weight, time, dose, etc. is meant to encompass variations of ±2%, even more preferably ±1%, and still more preferably ±0.1% from the specified amount, as such variations are appropriate to perform the disclosed method.

As used herein, the terms "biological marker" and "biomarker" are used interchangeably and carry the meaning as understood by one of ordinary skill in the art. The term specifically encompasses a testable or measurable indicator that can be linked or associated with a phenotype or trait. The indicator can be enzymatic, genetic, biochemical, physiological, or other form as known in the art.

As used herein, the term "ACE/vasopeptidase inhibitor" means an inhibitor of ACE and/or an inhibitor of vasopeptidase. Thus, an ACE/vasopeptidase inhibitor can comprise an ACE inhibitor and/or a combined ACE and NEP inhibitor.

As used herein, the term "ACE inhibitor" means an inhibitor of angiotensin converting enzyme (ACE).

As used herein, the term "health care provider" is known in the art and specifically includes a physician, a person with authority to prescribe a medication (whether directly or indirectly), and a veterinarian. In certain embodiments, a health care provider includes an individual that provides a medication without prescription, such as in providing an over-the-counter medication.

As used herein, the terms "identifying subjects" and "diagnosing" are used interchangeably with regard to the detection of a "predisposition", "increased propensity", "risk", "increased risk", and the like. The terms specifically encompass identifying the propensity for a subject to develop ACE/vasopeptidase inhibitor associated angioedema.

As used herein, the terms "standard", "normal range", "control range", and "clinical range" have normal meanings as known in the art. As used herein, these terms do not apply to DPP IV or APP enzyme activity in populations that have ACE/vasopeptidase inhibitor associated angioedema at the time of detection or measurement. The terms "subject range" or "experimental range" and the like are descriptive of enzyme activity ranges in subjects or patients with ACE/vasopeptidase inhibitor associated angioedema (acute or in the patient history). One of ordinary skill in the art can determine the clinical ranges for a given population and numerous clinical ranges and standards are known in the art for a variety of enzyme activities.

As used herein, the terms "vasopeptidase enzyme" and "vasopeptidase" are used interchangeably and include, but are not limited to, angiotensin-converting enzyme (ACE) and neutral endopeptidase (NEP). Other vasopeptidases will be known to those with skill in the art.

As used herein, the term "vasopeptidase inhibitor" includes, but is not limited to, compounds that inhibit both ACE and neutral endopeptidase (NEP).

As used herein, the term "ACE/vasopeptidase inhibitor" means an ACE inhibitor and/or a vasopeptidase inhibitor.

As used herein, the term "contraindicated" means a symptom or condition that makes a treatment, procedure, or administration of a medication inadvisable.

As used herein, the terms "detecting" and "detect" are used interchangeably and mean qualitative and/or quantitative determinations, including measuring an amount of enzyme activity in terms of units of activity or units activity per unit time, and the like.

As used herein, the terms "standard dipeptidyl peptidase IV activity" and "standard aminopeptidase P activity" mean an activity that represents an average measurement of the APP and DPP IV activities of a number of individuals. The activities can be measured by employing activity assays such as those disclosed herein. A standard activity can be employed as a benchmark against which an activity observed in a sample is gauged.

As used herein, the term "angioedemic condition" means a condition in a subject comprising at least the onset of symptoms consistent with a clinical diagnosis of angioedema. An angioedemic condition can comprise symptoms and effects peripherally associated with angioedema or symptoms and effects arising as a result of the onset or presence of angioedema.

The term "subject" as used herein refers to any invertebrate or vertebrate species. The methods of the present invention are particularly useful in the treatment of warm-blooded vertebrates. Thus, in a preferred embodiment, the invention concerns mammals and birds.

II. General Considerations

Angiotensin-converting enzyme (ACE) inhibitors and vasopeptidase inhibitors are indicated for the treatment of hypertension, congestive heart failure, diabetic neuropathy, coronary artery disease, and certain other conditions. In addition, considerable research efforts are ongoing to further improve treatment of these conditions with ACE and vasopeptidase inhibitors and to identify new inhibitors. These are medically important drugs with large markets for the treatment of humans and other mammals.

The present invention provides biological markers, diagnostic tests, assays, kits, and pharmaceutical indications which are useful for identifying individuals susceptible to developing angioedema associated with treatment by an angiotensin converting enzyme (ACE) inhibitor or a vasopeptidase inhibitor. The markers, tests, assays, kits and indications described herein, are generally applicable to humans and other mammals.

It will be understood that the methods and articles of the present invention can be employed to identify subjects or individuals that are compatible with administration of ACE/vasopeptidase inhibitors. For these subjects, ACE/vasopeptidase inhibitor treatment might be indicated depending on their need for such treatment as determined by one of ordinary skill in the art.

II.A. Angiotensin Converting Enzyme

Figure 2:
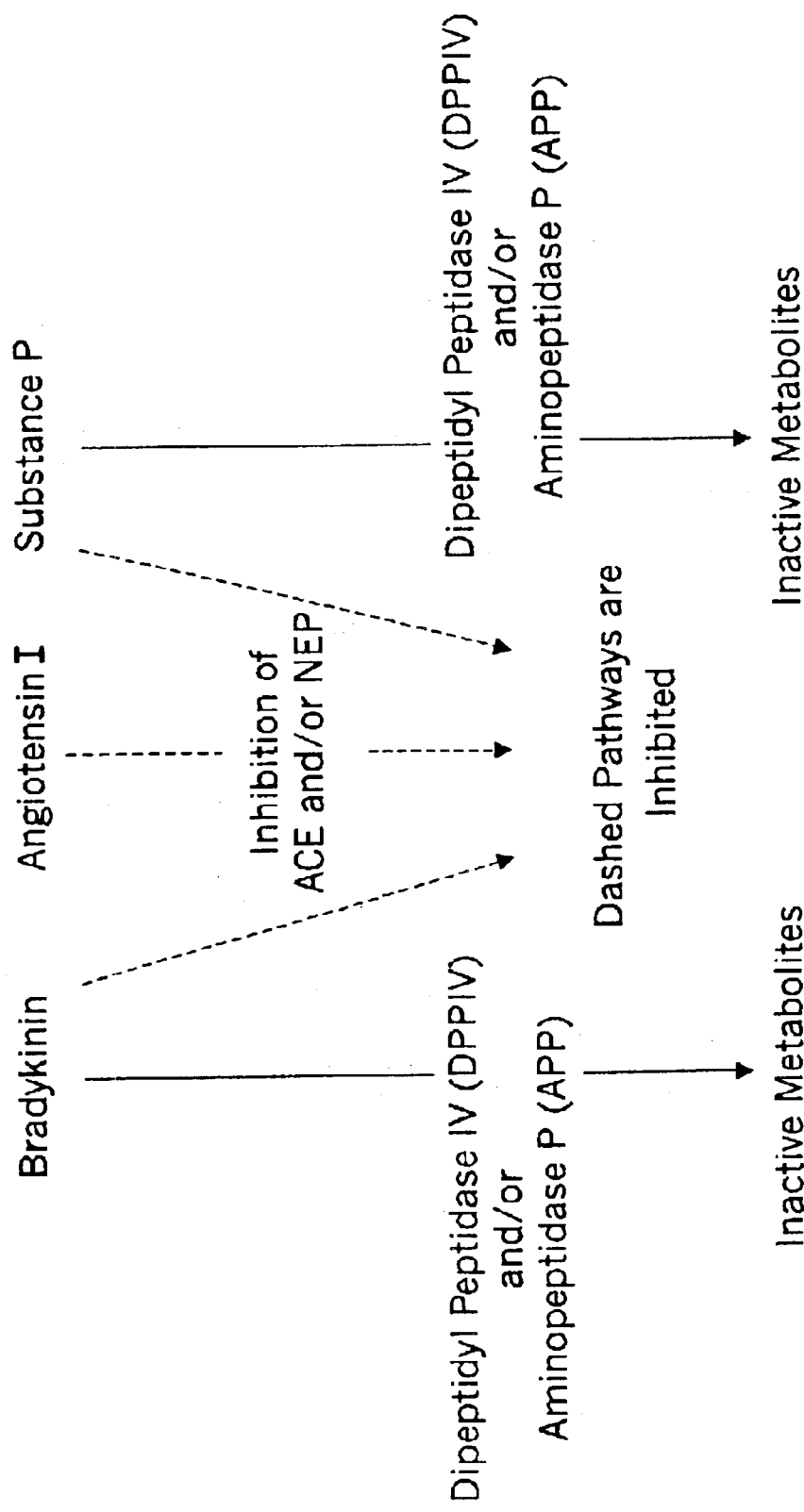
FIG. 2 is a diagram depicting an overview of angiotensin-converting enzyme (ACE) inhibitor and neutral endopeptidase (NEP) inhibitor action on the systems/pathways described in FIG. 1.

Angiotensin-converting enzyme (ACE) catalyzes the cleavage of angiotensin I into angiotensin II, which has an activity of raising blood pressure (see FIG. 1). ACE and NEP catalyze the degradation of bradykinin and substance P into inactive metabolites. NEP also catalyzes the degradation of atrial natriutetic peptide (ANP) into inactive metabolites. In contrast to angiotensin II, bradykinin and ANP have an activity of lowering blood pressure. Therefore, the use or administration of an ACE/vasopeptidase inhibitor generally results in a reduction in blood pressure because these inhibitors reduce angiotensin II production and increase bradykinin and/or ANP concentrations by inhibiting their degradation into inactive metabolites (see FIG. 2). Included in the many additional applications of ACE inhibitors are the treatment of cardiac diseases, renal diseases, and diabetes. Vasopeptidase inhibitors are also under investigation for use in these conditions and are awaiting regulatory approval. The clinical effectiveness of these inhibitors might result from influences on multiple physiological pathways, however, and the present invention is in no way bound by theory or mechanism.

Figure 3:
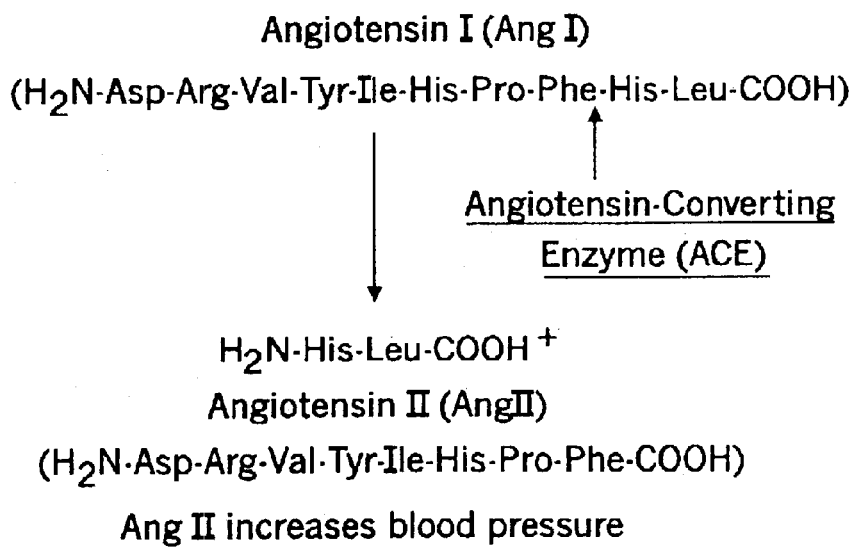
FIG. 3 is a diagram depicting the catalysis of angiotensin I to angiotensin II by ACE and includes the amino acid residue sequence (SEQ ID NOs:1 and 2) of each species and the major position for enzymatic cleavage of the angiotensin I amino acid residue chain.

The ACE enzymatic pathway is the primary pathway for angiotensin II formation and bradykinin degradation (see FIG. 3). Alternative pathways have been identified for the degradation of both bradykinin and substance P, however (see FIGS. 4A and 4B). These pathways comprise the degradation of bradykinin by the aminopeptidase P (APP) and dipeptidyl peptidase IV (DPP IV) enzymes, and the degradation of substance P by DPP IV. In general, the contribution of the alternative DPP IV and APP pathways could, but not necessarily, increase during ACE/vasopeptidase inhibition for individuals that are at a reduced risk of angioedema ("non-ACEI") even in comparison to normotensives ("Control", see FIG. 5). On the other hand, individuals with increased angioedema risk ("ACEI-associated") show a reduction alternative pathway activity (for example, DPP IV).

II.B. Angiotensin Converting Enzyme and Vasopeptidase Inhibitors

As noted, ACE acts on converting angiotensin I to angiotensin II. Angiotensin II increases blood pressure and is considered a main cause of essential hypertension. A variety of studies have been directed to substances inhibiting ACE actions, primarily addressing the suppression of a rise in blood pressure.

Therapeutic vasodepressors such as CAPTOPRIL™ and D-2-methyl-3-mercaptopropanoyl-L-proline have been synthesized as ACE inhibitors. Additional ACE inhibitors available commercially include ENALAPRIL™, ENALAPRILAT™, QUINAPRIL™, RAMIPRIL™, CILAZAPRIL™, DELAPRIL™, FOSENOPRIL™, ZOFENOPRIL™, INDOLAPRIL™, LISINOPRIL™, PERINDOPRIL™, SPIRAPRIL™, PENTOPRIL™, PIVOPRIL™, and known pharmaceutically acceptable salts thereof. From foodstuff, peptides having ACE inhibiting activities have been separated through enzymatic hydrolysis of casein (Japanese Laid-Open Patent Publication Nos. 62-270533, 64-5497, 64-83096) and soybean protein (Japanese Laid-Open Patent Publication Nos. 3-1671981).

Synthetic ACE inhibitors exhibit strong activities, and can exhibit adverse effects (such as angioedema). ACE inhibitory peptides derived from casein or soybean protein have been developed with expectation of low toxicity and high safety, even though they exhibit low activities. Recent studies, therefore, have been focused on separating ACE inhibitors from foodstuff materials and manufacturing them on a large scale by chemical synthetic methods.

An ACE inhibitor derived from food protein was first reported in 1979 by Oshima et al. (Oshima et al., (1979) *Biochim. Biophys. Acta* 556: 128). Since then over 40 ACE inhibitory peptides have been disclosed to date (see, e.g., Ariyoshi, (1993) *Trends Food Sci. Tech*., May, 1993, p. 139). A number of ACE inhibitory peptides have been derived from foodstuff such as sour milk (Nakamura et al., (1995) *J. Dairy Sci.* 78: 777), tuna tissue (Kohama et al., (1988) *Biochem. Biophys. Res. Comm.* 155(1): 332), sardine muscle (Matsuda et al., (1992) *Nippon Nogeigaku Kaishi* 66(11): 1645), oyster protein (Matsumoto et al., (1994) *Nippon Shokuhin Kogyo Gakkaishi* 41(9): 589), *Ficus carica* (Maruyama et al., (1989) *Agric. Biol. Chem.* 53(10): 2763), and rice (Muramoto & Kawamora, (1991) *Food Ind.* 34(11): 18). Furthermore, numerous patent applications have been filed in relation with ACE inhibitory peptides, including synthesized inhibitors as well as those isolated from natural products See e.g., U.S. Pat. Nos. 5,449,661; 5,071,955; 4,692,459; 4,585,758; 4,512,979; 4,191,753; 3,832,337; and European Patent No. EP174162.

II.C. Angioedema

It has been observed that treatment with ACE/vasopeptidase inhibitors is associated with the development of angioedema in a small percentage of individuals. The affected population accounts for approximately 0.1% to approximately 1.0% of patients receiving treatment with ACE/vasopeptidase inhibitors and appears to be more prevalent among African Americans than Caucasian Americans.

In general, angioedema is a swelling of tissue and especially affects the lips and other parts of the mouth, throat, larynx, eyelids, genitals, hands, and feet. Angioedema of the mouth, tongue and larynx can be life threatening especially when severe swelling makes breathing difficult.

The present inventor has discovered that deficiencies in the dipeptidyl peptidase IV (DPP IV) and aminopeptidase P (APP) enzymatic pathways are related to vasopeptidase inhibitor associated angioedema. For example, the present inventor discovered that DPP IV and/or APP activity is reduced in individuals with ACE associated angioedema compared to activity in patients with hypertension who have been treated with an ACE inhibitor but have not had angioedema.

III. Biological Markers

The present invention provides biological markers (also known as biomarkers) for identifying subjects or individuals with a susceptibility to ACE/vasopeptidase inhibitor associated angioedema. For example, as described herein, a low DPP IV serum enzymatic activity is associated with an increased risk that an individual will develop angioedema if an ACE/vasopeptidase inhibitor is administered. In another example, as described herein, a low APP serum enzymatic activity is associated with an increased risk that an individual will develop angioedema if an ACE/vasopeptidase inhibitor is administered. Thus, biological markers specifically encompasses a testable or measurable indicator that can be linked or associated with a phenotype or trait. The indicator can be enzymatic, genetic, biochemical, physiological, or other form as known in the art. Summarily, a biological marker or a biomarker demonstrates a correlation between a first condition and a second condition.

In one aspect of the present invention, dipeptidyl peptidase IV (DPP IV) activity is a biological marker for ACE/vasopeptidase inhibitor associated angioedema. In another aspect of the present invention, aminopeptidase P (APP) activity is a biological marker for ACE/vasopeptidase inhibitor associated angioedema. In general, the activity of either enzyme is preferably detected in a biological sample of the subject, and more preferably a serum sample. In certain embodiments, other useful biological samples include, but are not limited to: tissue, biopsy, interstitial fluid, feces, urine, whole blood, and epithelium. The biological samples can be collected and processed according to methods known in the art for measuring enzymatic activity (or with adaptations as would be apparent from the disclosure hereof).

In certain embodiments, the level of enzymatic activity can be measured qualitatively and, in other embodiments, the level of enzymatic activity can be measured quantitatively. In certain embodiments for the evaluation of ACE/vasopeptidase inhibitor associated angioedema, DPP IV activity can be measured and analyzed; in other embodiments APP activity can be measured and analyzed; and in yet other embodiments, both DPP IV and APP activities can be measured and analyzed. The same is true for qualitative detection of the biological markers. Several assays are described in the Examples. In general, a qualitative assay can include a reaction substrate that is placed in the biological sample and reacted with the DPP IV and/or APP enzyme present in the sample. The reaction substrate can change colors, for example, if the examined activity is too low/high by a relative amount, and a color change can indicate detection of activity. The reaction substrate can be compared to a similar substrate preparation reacted with a control or standard. In certain embodiments, DPP IV and/or APP enzymatic activity in a biological sample obtained from a subject can be measured in vitro and in other embodiments, it can be measured in vivo. In general, the measured activity is inversely proportional to the risk for ACE/vasopeptidase inhibitor associated angioedema. Laboratory Example 1 demonstrates the use of DPP IV as a biological marker in the context of the present invention.

In certain embodiments, a health care professional can test a subject for risk for developing an ACE/vasopeptidase inhibitor associated angioedema by a method comprising: detecting or measuring a serum DPP IV and/or APP activity; administering the ACE/vasopeptidase inhibitor for a time sufficient to inhibit ACE and/or NEP activity; and then detecting or measuring the serum DPP IV and/or APP activity again, for example, after a period of time has lapsed.

In certain aspects of this embodiment, an increase in DPP IV and/or APP activity indicates that the subject has a low risk for developing ACE/vasopeptidase inhibitor associated angioedema. In certain other embodiments, a decrease in DPP IV and/or APP activity indicates that the subject has a high risk for developing ACE/vasopeptidase inhibitor associated angioedema. In yet other aspects of this embodiment, a DPP IV and/or APP activity that does not significantly change indicates that the subject has an intermediate to high risk for developing ACE/vasopeptidase inhibitor associated angioedema.

A subject's risk of developing an angioedemic condition can be analyzed at any time, for example, when considering administering an ACE/vasopeptidase inhibitor to the subject or after the administration has commenced. Also, the diagnostic tests described herein (which can rely on one or more biological markers) can be employed to evaluate the cause of angioedema in a patient that is currently taking an ACE/vasopeptidase inhibitor.

IV. ACE Inhibitors and Vasopeptidase Inhibitors

ACE inhibitors can differ in the chemical structure of their active moieties, in potency, in bioavailability, in plasma half-life, in route of elimination, in their distribution and affinity for tissue-bound ACE, and in whether they are administered as prodrugs. The same can be true for vasopeptidase inhibitors. Those of ordinary skill in the art recognize that the side effects of ACE inhibitors can be divided into those that are class specific and those that relate to specific agents. ACE inhibitors decrease systemic vascular resistance without increasing heart rate and they promote natriuresis. ACE inhibitors have proved effective in the treatment of hypertension. ACE inhibitors also decrease mortality in congestive heart failure and left ventricular dysfunction after myocardial infarction, and they delay the progression of diabetic nephropathy.

Certain examples of known and commercially available ACE inhibitors are listed in Table 1. This is not meant to be an exhaustive list, but merely exemplary of certain ACE inhibitors that can be employed in treating subjects in need of treatment therewith. An example of a vasopeptidase inhibitor in development includes omapatrilat (brand name VANLEV™ by Bristol-Meyers Squibb).

TABLE 1

Marketed ACE Inhibitors

| Compound Name (Generic Drug) | Brand Name | Company (Maker of Brand Name) |
| --- | --- | --- |
| Captopril | CAPOTEN | |
| Enalapril | VASOTEC | Merck |
| Lisinopril | ZESTRIL | Zeneca |
| Lisinopril | PRINIVIL | Merck |
| Benazepril | LOTENSIN | Novartis |
| Quinapril | ACCUPRIL | Parke-Davis |
| Ramipril | ALTACE | Monarch |
| Trandolapril | MAVIK | Knoll (Roussel Uclaf) |
| Moexipril | UNIVASE | Schwartz |

TABLE 1-continued

Marketed ACE Inhibitors

| Compound Name (Generic Drug) | Brand Name | Company (Maker of Brand Name) |
|---|---|---|
| Fosinopril | MONOPRIL | BMS |
| Perindep | ACESRI | Solva |

V. ACE/Vasopeptidase Inhibitor-Associated Angioedema

ACE inhibitors have been shown to reduce mortality in patients with congestive heart failure, diabetic nephropathy, and coronary artery disease. In addition to ACE inhibitor-produced effects in reducing angiotensin II production, evidence from both animal studies and human studies indicate that cardioprotective effects of ACE inhibitors derive in part through potentiation of the effects of bradykinin (Gainer et al., (1998) *New Engl. J. Med.* 339: 1285–92, incorporated herein by reference). Another group of drugs have been identified with combined ACE/NEP inhibitory effects (these drugs are included in the meaning of the term "vasopeptidase inhibitors"), that block degradation of bradykinin and substance P through two pathways and also block the degradation of atrial natriutetic peptide (ANP). These combined ACE/NEP inhibitor medications appear to be particularly effect in lowering blood pressure in hypertensive African Americans.

While it is not the inventor's desire to be bound to theory or mechanism, it is postulated that some aspect of bradykinin and/or substance P plays a role in potentiating angioedema (Emanueli et al., (1998) *Hypertension* 31:1299–1304; Kim et al., (2000) *J. Pharm. Exp. Ther.* 292: 295–298; Ersahin et al., (1997) *J. Cardiovasc. Pharm.* 30: 96–101; Blais et al., (1999) *Immunopharmacology* 43: 293–302; Blais et al., (1999) *Peptides* 20: 421–430; Damas et al., (1996) *N-S Arch. Pharmacol.* 354: 662–669, all of which are incorporated herein by reference). For example, an over accumulation of bradykinin and/or substance P might help potentiate ACE/vasopeptidase inhibitor associated angioedema. Thus, using this example, it is postulated by the inventor that inhibition of bradykinin and/or substance P breakdown by ACE or combined ACE/NEP inhibitor action has beneficial effects up to a point; however, certain individuals appear to have an inability to clear an excessive accumulation of bradykinin and/or substance P leading to an increased risk of developing angioedema.

The risk of ACE inhibitor-associated angioedema is increased in African Americans compared to Caucasians, suggesting that genetic factors can modulate risk of angioedema (Brown et al., (1996) *Clin. Pharmacol. Ther.* 60: 8–13, incorporated herein by reference). Also, the inventor has observed that there is a large number of transplant recipients among the patients with angioedema. Again, without being bound to any theory or mechanism, the inventor hypothesizes that cyclosporin A, which is commonly used to treat transplant patients and also inhibits serum DPP IV activity (Scharpe et al., (1990) *Clin. Chem.* 36: 984), results in ACE/vasopeptidase inhibitor associated angioedema in transplant recipients. Thus, a genetic and/or an acquired defect in the aminopeptidase P and/or dipeptidyl peptidase IV pathways, which serve as alternative pathways for the degradation of bradykinin and substance P, are described herein to predispose patients to the development of ACE inhibitor or vasopeptidase inhibitor angioedema.

VI. Peptide, Polypeptide and Polynucleotide Components of the Present Invention

A variety of biological information including nucleotide and peptide sequence information is available from public databases provided, for example, by the National Center for Biotechnology Information (NCBI) located at the United States National Library of Medicine (NLM). The NCBI is located on the world wide web at the URL "http://www.ncbi.nlm.nih.gov/" and the NLM is located on the world wide web at the URL "http://www.nlm.nih.gov/". The NCBI website provides access to a number of scientific database resources including: GenBank, PubMed, Genomes, LocusLink, Online Mendelian Inheritance in Man (OMIM), Proteins, and Structures. A common interface to the polypeptide and polynucleotide databases is referred to as Entrez which can be accessed from the NCBI website on the World Wide Web at URL "http://www.ncbi.nlm.nih.gov/Entrez/" or through the LocusLink website.

The following subsections disclose a plurality of molecules that can form an element of the present invention. This discussion is not meant to be an inclusive list of molecules that can form a component of the present invention. The following subsections are included to provide additional detail regarding components of the present invention, as well as to help illustrate how the various molecules relate to one another in vivo.

VI.A. Angiotensin I and Angiotensin II

The following summary is available in the NCBI LocusLink database:

The human AGT gene product, pre-angiotensinogen, is expressed in the liver and is cleaved by the enzyme renin in response to lowered blood pressure. The resulting product, angiotensin I is then cleaved by angiotensin converting enzyme (ACE) to generate the physiologically active enzyme [sic, peptide] angiotensin II. Human pre-angiotensinogen is encoded by two mRNAs that differ only in the length of the 3'-untranslated region due to postulated use of two polyadenylation sites. There may also be alternative initiation codons (nucleotides 40–42 and 67–69). AGT is involved in maintaining blood pressure and in the pathogenesis of essential hypertension and preeclampsia.

The *Homo sapiens* Official Gene Symbol and Name is: AGT: angiotensinogen. In a preferred embodiment of the present invention, angiotensin I comprises the amino acid sequence of SEQ ID NO: 1. The hormone angiotensin II is recognized as one of the most potent vasopressor agents that produces hypertension in mammals. The action of the enzyme renin on the plasma protein substrate angiotensinogen results in the production of an inactive decapeptide, angiotensin I, which upon conversion by the non-selective angiotensin converting enzyme (ACE) provides angiotensin II, the active hormone. See e.g., Regoli et al., (1974) *Pharm. Rev.* 26: 69.

Angiotensin II causes vasoconstriction and stimulates aldosterone secretion (from the adrenal gland) that results in a rise of both blood volume and pressure. Inhibitors of angiotensin II are therefore useful in treating hypertension, congestive heart failure, renal insufficiency associated with diabetic or hypertensive nephropathy, and glaucoma. See e.g., Garrison et al., in *The Pharmacological Basis of Therapeutics*, 8th Edition, (Gilman, Goodman, Rall, Nies, and Taylor, eds), Pergamon Press, New York, 1990: p. 761–762; and Dzau, (1991) *New Engl. J. Med.* 324: 1124–1130.

Angiotensin II also can act on other organs such as the brain (Fitzsimmons, (1980) *Rev. Physiol. Biochem. Pharmacol.* 87: 117). Antagonists of angiotensin II are therefore useful in enhancing cognitive performance in patients affected by conditions such as age associated mental impairment or Alzheimer's disease, and in treating cognitive disorders such as anxiety. See e.g., Dennes et al., (1992) *Brit. J. Pharmacol.* 105: 88; and Barnes et al., (1991) *FASEB J.*, 5: 678.

In addition, angiotensin II acts on a variety of glandular tissues including the kidney, liver, and ovaries. Antagonists of angiotensin II are useful in treating conditions, disorders, or diseases of these tissues associated with excessive or unregulated angiotensin II activity. Antagonists of angiotensin II are also useful in treating kidney damage due to non-steroidal antiinflammatory agents.

Angiotensin II has a role in regulation of the rate of cell growth and differentiation. Inhibitors of angiotensin II are therefore useful in treating disorders marked by excessive cell proliferation such as restenosis. See, e.g., Naftilan et al., (1989) *J. Clin. Invest.* 83: 1419, Kauffman et al., (1991) *Life Sci.* 49: 223–228, and Jackson et al., (1988) *Nature* 335: 437. Angiotensin II is formed in the human body through proteolysis of angiotensin I (Ang I) primarily through the action of angiotensin-converting enzyme (see FIG. 1). In a preferred embodiment of the present invention, angiotensin II comprises the amino acid sequence of SEQ ID NO: 2.

VI.B. Bradykinin

Bradykinin is a nonapeptide generated as a result of the activity of kallikreins, a group of proteolytic enzymes present in most tissues and body fluids, on kininogens. Once released, kinins produce many physiological responses, including pain and hyperanalgesia by stimulating C- and A-fibers in the periphery. There is also considerable evidence that kinins contribute to the inflammatory response.

Bradykinin, and its physiologically important related peptides kallidin (Lys-bradykinin) and Met-Lys-bradykinin, exhibit physiological actions which qualify them as mediators of inflammatory reactions, hypotensive states, and pain. Bradykinin is overproduced in pathological conditions such as septic shock, anaphylaxis, rhinitis, asthma, inflammatory bowel disease, and certain other conditions including acute pancreatitis, post-gastrectomy dumping syndrome, carcinoid syndrome, migraine, and angioneurotic edema. The production of bradykinin from the plasma results in pain at the site of the pathological condition, and the overproduction intensifies the pain directly or via bradykinin-induced activation of the arachidonic acid pathway which produces prostaglandins and leukotrienes, the more distal and actual mediators of inflammation.

In addition to its analgesic and proinflammatory effects, bradykinin is a vasodilator. Because of its ability to lower blood pressure, bradykinin has been implicated in the pathogenesis of several shock syndromes, particularly septic or endotoxic shock. Bradykinin is also a potent bronchoconstrictor in animals and asthmatic subjects and it has been implicated as a contributor to the pathogenesis of airway inflammatory conditions such as allergic asthma and rhinitis. In a preferred embodiment of the present invention, bradykinin comprises the amino acid sequence of SEQ ID NO: 3

Summarily, bradykinin increases vascular permeability, dilates blood vessels, increases blood flow, contracts non-vascular smooth muscle (e.g., bronchial), stimulates pain, and lowers blood pressure (hypotensive). These are also cardinal signs of inflammation. Bradykinin is formed by the cleavage of kininogen by the enzyme kallikrein, and is rapidly cleared in the mammalian body by cleavage into inactive metabolites (see FIG. 1) primarily by angiotensin-converting enzyme (ACE) and neutral endopeptidase (NEP).

VI.C. Substance P

Substance P is a naturally occurring undecapeptide belonging to the tachykinin family of peptides, the latter being so-named because of their prompt stimulatory action on smooth muscle tissue. More specially, substance P is a pharmaceutically active neuropeptide that is produced in mammals (having originally been isolated from gut) and possesses a characteristic amino acid sequence that is illustrated by Veber et al. in U.S. Pat. No. 4,680,283. The wide involvement of substance P and other tachykinins in the pathophysiology of numerous diseases has been amply demonstrated in the art. For instance, substance P has recently been shown to be involved in the transmission of pain or migraine, as well as in central nervous system disorders such as anxiety and schizophrenia, in respiratory and inflammatory diseases such as asthma and rheumatoid arthritis, respectively, and in gastrointestinal disorders and diseases of GI tract, like ulcerative colitis and Crohn's diseases, etc. It is also reported that the tachykinin antagonists are useful for the treatment of allergic conditions, immunoregulation, vasodilation, bronchospasm, reflex or neuronal control of the viscera and senile dementia of the Alzheimer's type, emesis, sunburn and *Helicobacter pylori* infection.

Substance P is similar to bradykinin in function in that substance P stimulates: smooth muscle contraction, inflammation, and blood vessel dilation. Substance P also functions in neurotransmission, histamine release, and activation of the immune system. Substance P is synthesized in neurons and, similar to bradykinin, is degraded into inactive metabolites by ACE and NEP. In a preferred embodiment of the present invention, substance P comprises the amino acid sequence of SEQ ID NO: 4.

VI.D. Dipeptidyl Peptidase IV (DPP IV)

Dipeptidyl peptidase IV (DPPIV) is a serine protease that cleaves N-terminal dipeptides from a peptide chain containing, preferably, a proline residue in the penultimate position. Although the biological role of DPP-IV in mammalian systems has not been completely established, it is believed to play an important role in neuropeptide metabolism, T-cell activation, attachment of cancer cells to the endothelium, and the entry of HIV into lymphoid cells.

Various types of dipeptidyl peptidase IV have been purified and the enzymological properties have been revealed. For example, the dipeptidyl peptidase IV is isolated from rat liver (Hopsu-Havu & Glenner, (1966) *Histochem.* 7: 197–201), swine kidney (Barth et al., (1974) *Acta Biol. Med. Chem.* 32:157–174), small intestine (Svensson et al., (1978) *Eur. J. Biochem.* 90: 489–498), liver (Fukasawa et al., (1981) *Biochim. Biophys. Acta* 657: 179–189), human submaxillary gland (Oya et al., (1972) *Biochim. Biophys. Acta* 258: 591–599), sheep kidney (Yoshimoto & Walter, (1977) *Biochim. Biophys. Acta*, 485: 391–401; Yoshimoto et al., (1978) *J. Biol. Chem.* 253: 3708–3716) or microorganisms (Fukusawa & Harada, (1981) *Arch. Biochem. Biophys.* 210: 230–237; Yoshimoto & Tsuru, (1982) *Biochem.* 91:1899–1906).

Figure 4A:
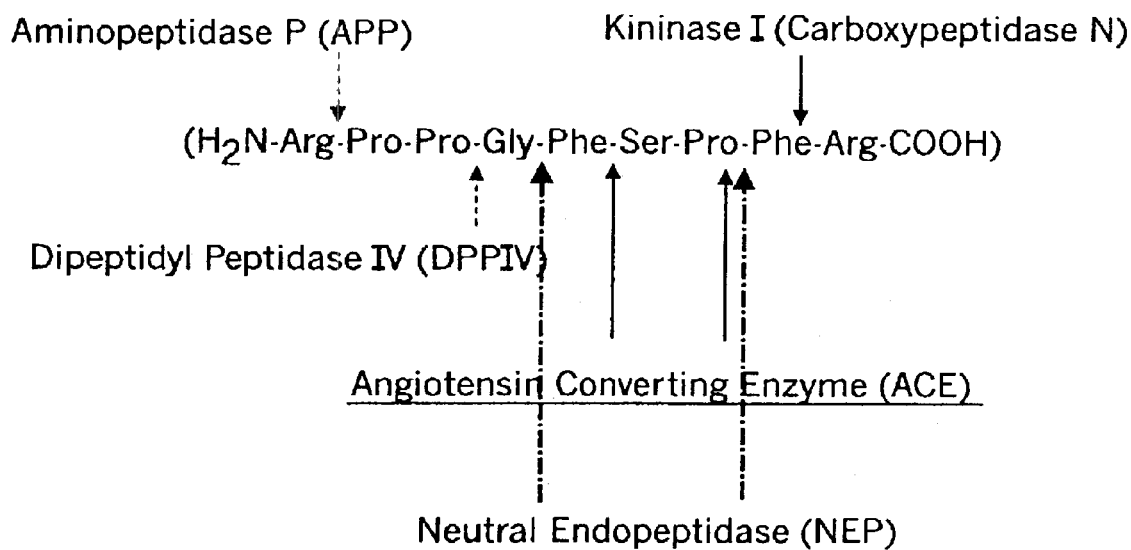
FIG. 4A is a diagram depicting the catalysis of bradykinin (SEQ ID NO:3) into inactive metabolites by ACE and NEP (arrows depict the sites of enzymatic cleavage; cleavage sites of the dipeptidyl peptidase IV (DPP IV) and aminopeptidase P (APP) pathways for the degradation of bradykinin into inactive metabolites are indicated by dashed arrows).
Figure 4B:
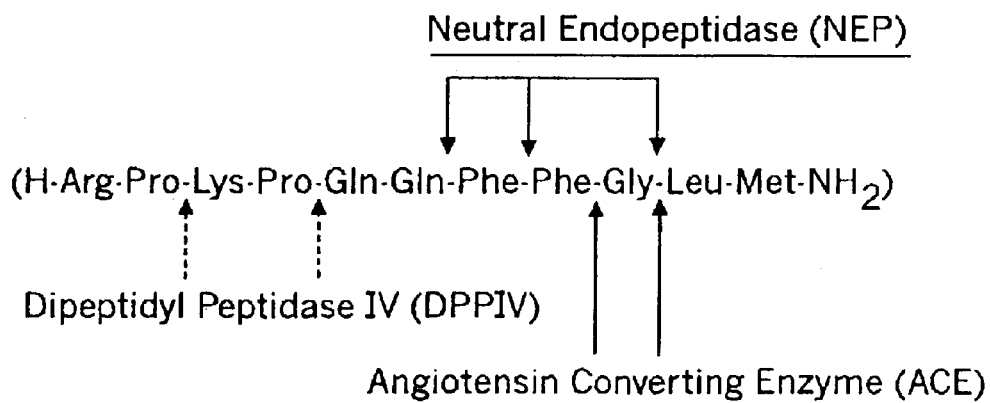
FIG. 4B is a diagram depicting the catalysis of substance P (SEQ ID NO:4) by ACE and NEP. The arrows depict the sites of enzymatic cleavage (a cleavage site of the DPP IV pathway for the degradation of substance P into inactive metabolites is indicated by a dashed arrow).

The DPP IV enzyme is a serine exopeptidase that cleaves X-proline dipeptides from the N-terminus of polypeptides. It is an intrinsic membrane glycoprotein anchored into the cell membrane by its N-terminal end. Soluble forms of DPP IV are also known including those in the serum (Struvf et al., (1999) *J. Immunol.* 162: 4903–4909, incorporated herein by reference). High levels of DPP IV enzyme are found in the brush-border membranes of the kidney proximal tubule and of the small intestine, but several other tissues also express the enzyme. DPP IV cleaves bradykinin and substance P into inactive (or reduced activity) metabolites as shown in FIGS. 4A and 4B. Table 2 discloses additional embodiments of DPP IV.

TABLE 2

Embodiments of GenBank Sequences for DPP4
(DPP4 is generally referred to herein as DPP IV)

| Nucleotide | Type | Protein |
|---|---|---|
| AH005372 | g | AAB60646 |
| U13710 | g | AAB60646 |
| U13711 | g | AAB60646 |
| U13712 | g | AAB60646 |
| U13713 | g | AAB60646 |
| U13714 | g | AAB60646 |
| U13715 | g | AAB60646 |
| U13716 | g | AAB60646 |
| U13717 | g | AAB60646 |
| U13718 | g | AAB60646 |
| U13719 | g | AAB60646 |
| U13720 | g | AAB60646 |
| U13721 | g | AAB60646 |
| U13722 | g | AAB60646 |
| U13723 | g | AAB60646 |
| U13724 | g | AAB60646 |
| U13725 | g | AAB60646 |
| U13726 | g | AAB60646 |
| U13727 | g | AAB60646 |
| U13728 | g | AAB60646 |
| U13729 | g | AAB60646 |
| U13730 | g | AAB60646 |
| U13731 | g | AAB60646 |
| U13732 | g | AAB60646 |
| U13733 | g | AAB60646 |
| U13734 | g | AAB60646 |
| U13735 | g | AAB60646 |
| M74777 | m | AAA51943 |
| M80536 | m | AAA52308 |
| X60708 | m | CAA43118 |

VI.E. Aminopeptidase P

Aminopeptidase P is known to cleave the N-terminal amino acid from peptides that have a prolyl residue in the second position (Orawski et al., (1987) *Mol. Cell. Biochem.* 75: 123–132; Simmons & Orawski, (1992) *J. Biol. Chem.* 267: 4897–4903; Yoshimoto et al., (1994) *Arch. Biochem. Biophys.* 311: 28–34). It has been suggested that membrane-bound aminopeptidase P has an important role in vivo in the pulmonary degradation of bradykinin (Ryan et al., (1994) *J. Pharmacol. Exper. Thera.* 269: 941–947; Ryan, (1989) *Am. J. Physiol.* 257: L53–L60; Orawski (1987) *Mol. Cell. Biochem.* 75: 123–132; Orawski, (1989) *Adv. Exp. Med. Biol.* 2478: 355–364; Simmons & Orawski, (1992) *J. Biol. Chem.* 267, 4897–4903; Kitamura, (1995) *Br. J. Pharmacol.* 114: 6–7; Baker (1991) *Cir. Shock* 33: 37–47; Pesquero et al., (1992) *J. Hyperten.* 10: 1471–1478; Pasquero et al., (1992) *J. Hyperten.* 10: 1479–1484) by cleaving its $Arg^1$-$Pro^2$ bond. It has also been suggested that other peptidases could also play a role in bradykinin degradation (Orawski et al., (1989) *Adv. Exp. Med. Biol.* 2478: 355–364).

Several embodiments of the aminopeptidase P enzyme are useful in the present invention. Examples of useful embodiments are described herein, but are not meant to limit the present invention.

VI.E.1. Aminopeptidase P (Aminopeptidase 1, Soluble)

One embodiment is the APP referred to by Homo sapiens Official Gene Symbol and Name: XPNPEP1: X-prolyl aminopeptidase (aminopeptidase P) 1, soluble. Table 3 presents an additional embodiment of APP.

TABLE 3

Certain GenBank Sequences for Aminopeptidase P1

| Nucleotide | Type | Protein |
|---|---|---|
| AF195530 | m | AAF97866 |

VI.E.2. Aminopeptidase P (Aminopeptidase 2, Membrane-Bound)

Another useful embodiment is the APP referred to, in the NCBI LocusLink database, by Homo sapiens Official Gene Symbol and Name XPNPEP2: X-prolyl aminopeptidase (aminopeptidase P) 2, membrane-bound. Table 4 presents additional embodiments of APP2.

TABLE 4

Certain GenBank Sequences for Aminopeptidase P2

| Nucleotide | Type | Protein |
|---|---|---|
| AL023653 | g | CAA19220 |
| U90724 | m | AAB96394 |

VII. Dipeptidyl Peptidase IV Activity Assay

The present invention also comprises an assay for dipeptidyl peptidase IV. In a preferred embodiment, the steps for performing the assay are as follows. Initially, samples comprising 0, 25, 50 and 100 units (e.g., nM/ml) of p-nitroaniline are prepared for generating a standard curve. p-nitroaniline is a known substrate for DPP IV. The standard curve is generated by determining the absorbance of the standard solutions of p-nitroaniline at 405 nm and are plotted on a graph as concentration versus absorbance.

To perform a DPP IV assay on a sample obtained from a subject (e.g., a human serum sample), 20 µl of sample is incubated with 10 µl of 2 mM Gly-Pro-p-nitroanilide in 170 µM 0.1 M Tris-HC1 for 1 hour. The reaction is stopped by adding 800 µl sodium acetate (1 M, pH 4.5) and thee, absorbance is measured at 405 nm. The concentration of p-nitroaniline formed per ml per min is then calculated by employing a standard curve. The activity and/or presence of DPP IV in the sample can be determined by comparing the observed activity with a standard activity.

VIII. Aminopeptidase P Activity Assay

The present invention also comprises an aminopeptidase P activity assay. In a preferred embodiment, the steps for performing an APP assay are as follows. First, a calibration curve is prepared by monitoring fluorescence emission at 310 and 445 nm (excitation and emission wavelengths, respectively) from a range of concentrations of 1-arginine (0–5 mM).

Next, a sample is provided (e.g. a human serum sample). 20 µl of the sample is incubated at 37° C. with 180 µl HEPES buffer containing 5.6 mM Arg-Pro-Pro, yielding a final concentration of Arg-Pro-Pro of 0.5 mM. Arg-Pro-Pro is a known substrate for APP. After an incubation period of two hours, the reaction is stopped by adding 800 µl of cold, anhydrous ethanol to the reaction mixture. The mixture is then centrifuged at 2000×g at 4° C. for 15 minutes. The supernatant is decanted and incubated at room temperature with 3 ml of a revelation buffer. APP activity is calculated as nmoles arginine released per min per ml of serum sample.

IX. Applications of the Present Invention

The present invention can be employed in a range of applications. Preferably, the present invention is employed in a situation in which a physician is contemplating a course of treatment comprising an ACE inhibitor, a vasopeptidase inhibitor and combinations thereof. In this situation, the present invention can be employed to minimize the risk that a patient might develop an angioedemic condition.

The present invention can be employed, for example, to identify a subject that is susceptible to developing an angioedemic condition during a course of treatment which comprises administering an ACE inhibitor, a vasopeptidase inhibitor or, as is commonly the case, a combination thereof. The present invention can also be employed to determine if administration of an ACE inhibitor, a vasopeptidase inhibitor, or a combination thereof, is contraindicated for a subject. In a related application, the present invention can be employed in a method of screening a subject for compatibility with administration of a vasopeptidase. Additionally, the present invention can be marketed in the form of diagnostic kits, which a physician or a researcher can employ to identify a subject at risk for angioedema during a course of treatment which comprises administering an ACE inhibitor, a vasopeptidase inhibitor or, as is commonly the case, a combination thereof. These are just a few of the range of applications in which the present invention can be employed. These applications are described more fully herein below and in the Examples that follow.

IX.A. Method of Identifying a Subject that is Susceptible to Developing an Angioedemic Condition During a Course of Treatment An aspect of the present invention is the observation that there is a link between DPP IV and/or APP activity, ACE and/or vasopeptidase inhibitors and the onset of an angioedemic condition. Thus, when a subject is undergoing a course of treatment comprising administering an ACE inhibitor, a vasopeptidase inhibitor or a combination thereof, it is preferable to determine the activity of DPP IV and/or APP in a sample derived from the subject. Depressed DPP IV and/or APP activity levels indicate that the subject is at risk for developing an angioedemic condition as a result of the course of treatment.

In a preferred embodiment of this application of the present invention, a biological sample is initially provided by a subject. Preferably, the sample is a serum sample. A sample can be acquired from a subject by employing standard techniques, and will be dependent, in part, on the nature of the sample. For example, when the sample comprises a sample of the subject's blood, standard phlebotomic methods can be employed to acquire the sample, which can be further processed as required (e.g. isolating a serum component of sample).

Following sample acquisition and preparation (if required), a standard DPP IV and/or APP activity is determined. A standard DPP IV and/or APP activity can be determined by calculating DPP IV and/or APP activity in a control group of subjects. The number of subjects can vary, but preferably, the number of subjects is sufficiently large as to permit the identification of significant activity measurement. Similarly, the genetic qualities of the subjects can vary or can be held constant, at the preference of the researcher. This calculated activity can be employed as a standard (i.e. a standard DPP IV and/or APP activity), against which a subject's determined DPP IV and/or APP activity is gauged.

Subsequently, DPP IV and/or APP activity present in the sample can be determined. Both a standard DPP IV and/or APP, as well as DPP IV and/or APP activity present in a sample, can be measured by employing, for example, the activity assays disclosed herein, particularly in section VII (DPP IV activity) and in section VIII (APP activity).

When a value is determined for both a standard DPP IV and/or APP activity and DPP IV and/or APP activity present in a sample, the two values can be compared. If DPP IV and/or APP activity in the sample is found to be less than the activity of the control group (i.e., a standard activity) by about 10% or more, the subject is at risk for an angioedemic condition, should ACE and/or vasopeptidase inhibitor therapy be started or continued. Thus, ACE and/or vasopeptidase inhibitor therapy is contraindicated for subjects in which the DPP IV and/or APP activity of a sample is found to be less than the activity of the control group (i.e., a standard activity) by about 10% or more. On the other hand, ACE and/or vasopeptidase inhibitor therapy can be tolerated and/or indicated for subjects in which the DPP IV and/or APP activity of a sample is found to be within about 10% or less of the activity of the control group (i.e. a standard activity).

A 20% or more reduction in the DPP IV and/or APP activity in the biological sample, as compared to the standard DPP IV and/or APP activity also indicates that the subject is susceptible to developing an angioedema during a course of treatment comprising administering one of an ACE inhibitor and a vasopeptidase inhibitor. Additionally, a 30% or more reduction in the DPP IV and/or APP activity in the biological sample, as compared to the standard DPP IV and/or APP activity indicates that the subject is susceptible to developing an angioedema during a course of treatment comprising administering one of an ACE inhibitor and a vasopeptidase inhibitor.

IX.B. Method of Determining Contraindication for Administration of a Vasopeptidase Inhibitor, an ACE Inhibitor and Combinations Thereof In another aspect of the present invention, a vasopeptidate inhibitor, an ACE inhibitor and combinations thereof can be contraindicated if DPP IV and/or APP activity is found to fall outside the range of normal activities and/or amounts. APP and DPP IV activities can be determined by employing the assays disclosed in the present invention. In a preferred method of determining contraindication for administration of an ACE inhibitor or a vasopeptidase inhibitor to an individual, a biological sample obtained from a subject is initially provided. Preferably, the biological sample comprises serum and is obtained from a human subject, although the method can also be performed in the context of an organism other than a human and a sample can comprise a material other than serum.

Next, a standard DPP IV activity and/or APP activity can be determined and can be plotted to generate a standard curve. The standard DPP IV activity and/or APP activity can be determined by measuring a DPP IV and/or APP activity from a number of representative subjects. A standard DPP IV activity and/or APP activity measurement can serve as a benchmark against which a DPP IV activity and/or APP activity observed in a sample is measured.

Following providing (and preparing, if desired) a biological sample, a DPP IV activity and/or a APP activity for the biological sample can be determined. The DPP IV and/or APP activities can be determined as disclosed herein, and are preferably performed under the same conditions as were employed in generating the standard activity (i.e. the standard curve).

Observed DPP IV activity and/or APP activity in the biological sample can then be compared to the standard DPP IV activity and or APP activity. If the comparison indicates that DPP IV and/or APP activity in the biological sample is below the normal range, administration of an ACE or a vasopeptidase inhibitor can be contraindicated. Contraindication of administration of an ACE inhibitor or a vasopeptidase inhibitor can impart the beneficial effect of decreasing or eliminating the chance that a subject will develop an angioedemic condition.

IX.C. A Kit for Identifying a Subject at Risk for Angioedema During a Course of Treatment Comprising Administering an ACE Inhibitor, a Vasopeptidase Inhibitor or a Combination Thereof In another aspect of the present invention, a kit for identifying a subject at risk for angioedema during a course of treatment comprising administering an ACE inhibitor, a vasopeptidase inhibitor or a combination thereof is disclosed. Such a kit can be employed by a physician, laboratory researcher or other person desiring to identify an individual at risk for developing an angioedemic condition. In a preferred embodiment, the kit comprises a substrate for a DPP IV enzyme. Such a substrate preferably comprises gly-pro-p-nitroanilide; however, other substrates can be employed.

A kit of the present invention also preferable comprises a buffer, which can function to maintain pH and other conditions in an optimal range for a DPP assay. Any buffer adapted to maintain a set of desired conditions (e.g., pH, tonicity, etc) can be employed in a kit. A reaction stop solution is also preferably included in the kit. The reaction stop solution can be added to a reaction mixture in order to halt any DPP IV-catalyzed reaction occurring in the reaction mixture at a desired time point.

Additionally, a kit preferably comprises a set of instructions comprising information on a range of dipeptidyl peptidase IV activity in a control population. The information contained in such a set of instructions can advise a physician or researcher (or any person) who is employing the kit on the question of how to compare a DPP IV activity observed in a sample with a standard DPP IV activity. In other words, a set of instructions can advise the user of the kit how to interpret the results of a test performed by employing the kit. A set of instructions can also comprise step-by-step directions on how a user can employ the various components of the kit to generate an observed DPP IV activity from a sample. Thus, such a set of instructions can comprise information on volumes of solutions to be added, incubation time periods, wavelengths to monitor (if any) and other parameters of a DPP IV assay.

In practice, if an observed DPP IV activity falls within a range specified in a set of instructions, administering an ACE inhibitor, a vasopeptidase inhibitor or a combination thereof can be administered to a subject with the knowledge that the risk of the subject developing an angioedemic condition is minimal. Thus, such a kit can be employed to identify a subject at risk for developing an angioedemic condition before a course of treatment comprising administering a vasopeptidase inhibitor and/or an ACE inhibitor.

In another embodiment of a kit for identifying a subject at risk for angioedema during a course of treatment comprising administering an ACE inhibitor, a vasopeptidase inhibitor or a combination thereof, the kit comprises an APP substrate. A suitable APP substrate can comprise, for example, a peptide sequence comprising Arg-Pro-Pro. A dilution buffer can also be included and can be used to dilute a substrate solution or other concentrated solution supplied with the kit or derived from a sample acquired from a subject. A reaction stop solution can also be included, as well as a revelation buffer. The revelation buffer can assist in maintaining conditions under which APP activity in a sample can be determined. For example, if a calorimetric assay is employed, a revelation buffer can be employed to develop a degree of color. Alternatively, if a spectrophotometric assay is employed, the revelation buffer can be employed to maintain conditions under which a detectable reaction product can remain in a detectable state (i.e. undegraded).

Additionally, a set of instructions comprising information on a range of APP activity in a control population can be provided with a kit of the present invention. As described above in the context of DPP IV, if an observed APP activity falls within a range specified in a set of instructions, administering an ACE inhibitor, a vasopeptidase inhibitor or a combination thereof can be administered to a subject with the knowledge that the risk of the subject developing an angioedemic condition is minimal. Thus, such a kit can be employed to identify a subject at risk for developing an angioedemic condition before a course of treatment comprising administering a vasopeptidase inhibitor and/or an ACE inhibitor.

In yet another embodiment, a kit for identifying a subject at risk for angioedema during a course of treatment comprising administering an ACE inhibitor, a vasopeptidase inhibitor or a combination comprises an ACE inhibitor and/or a vasopeptidase inhibitor; and a packaging material comprising information that the vasopeptidase inhibitor is contraindicated for individuals with a serum DPP IV enzyme activity and/or a serum APP enzyme activity below a normal range, which can be specified in the packaging material.

IX.D. Method of Marketing a Vasopeptidase and/or an ACE Inhibitor

A method of marketing a vasopeptidase and/or an ACE inhibitor is also disclosed. In one embodiment, information about a diagnostic test adapted to identify a subject that is susceptible to angioedema as a result of taking the vasopeptidase inhibitor during a course of treatment comprising administering an ACE inhibitor, a vasopeptidase inhibitor, or a combination thereof is provided. When it is known that a given subject might be at risk for developing an angioedemic condition, this information can comprise an element of a marketing approach. In this way, a vasopeptidase and/or ACE inhibitor can be marketed to individuals who can tolerate these inhibitors, while subjects that might be susceptible to developing an angioedemic condition as a result of a course of treatment comprising these inhibitors can be advised of this risk.

This information can be presented to a consumer, whether the consumer is a physician or a subject, at the time an inhibitor is purchased. Alternatively, the information can be presented to a consumer at a point prior to purchase. This method of marketing can be advantageous because it is not only a marketing tool, but can also decrease the risk of a subject developing an angioedemic condition.

X. Illustrative Examples of Preferred Embodiments

This section of the present disclosure provides illustrative examples of the application of the present invention. The Illustrative Examples, therefore, provide additional guidance in the application of the present invention. These illustrative examples resemble medical case studies, since the present invention is preferably suited to therapeutic application (and therefore of particular benefit to physicians), in addition to being a valuable research tool. The Illustrative Examples are ordered similarly; first, facts of the case are presented, and subsequently, several outcomes are presented. These outcomes describe treatments a physician can recommend. In the Illustrative Examples, the physician in the examples arrives at his or her recommendation as a result of employing the present invention. In other words, the physician orders a test, which involves various aspects of the present invention (i.e. a determination of DPP IV activity, APP activity, etc). The physician then evaluates the results of the test and recommends a course of treatment. Thus, the alternative outcomes presented in the Illustrative Examples are based on the results of the test or tests ordered by the physician. The Illustrative Examples, therefore, serve to demonstrate how the present invention can be employed in a clinical setting.

ILLUSTRATIVE EXAMPLE 1

A 55-year-old African American woman smoker with diabetic nephropathy presents to clinic with poorly controlled hypertension. She is taking hydrochlorothiazide alone for treatment of her hypertension. Because of the patient's diabetic nephropathy the patient's physician determines that an ACE inhibitor is the drug of choice for treatment of her high blood pressure. However, based on demographic factors, the physician calculates that the patient's risk of ACE inhibitor-associated angioedema is high (1:400). (One of ordinary skill in the art is able to calculate an individual's risk based upon the scientific literature and the race of the patients.) He therefore draws blood for measurement of DPP IV activity and APP activity prior to starting her on an ACE inhibitor.

OUTCOME A OF ILLUSTRATIVE EXAMPLE 1

The patient's DPP IV and APP activities are found to be normal and she carries no genetic alleles associated with decreased activity. On this basis, the physician calculates that the patient's risk of angioedema is lower than predicted by demographics and starts her on an ACE inhibitor.

OUTCOME B OF EXAMPLE 1

The patient is found to have decreased DPP IV activity. On this basis her calculated risk of angioedema is unacceptably high and the physician chooses an alternative therapy.

ILLUSTRATIVE EXAMPLE 2

A 64-year-old African American man with dilated cardiomyopathy and a history of congestive heart failure presents to the emergency room with swelling of his lips and oropharynx. On examination he is noted to be stridorous and he is intubated to protect his airway. He is given intravenous corticosteroids and histamine $H_1$ and $H_2$ antagonists. Prior to admission he was taking the diuretic furosemide, the ACE inhibitor lisinopril, and the aldosterone receptor antagonist spironolactone. He has taken the ACE inhibitor for at least four years and has never had any previous episode of angioedema. Five days prior to admission he was started on the antibiotic ciprofloxacin for a urinary tract infection. It was not clear to the patient's physician whether his angioedema was related to his use of an ACE inhibitor. Given the proven benefit of ACE inhibitors as treatment in patients with left ventricular dysfunction, the physician desired to continue therapy, if possible. The physician draws blood samples for measurement of $C_1$ esterase inhibitor activity, APP and DPP IV activity, as well as a sample for extraction and analysis of DNA markers and sequences.

OUTCOME A OF ILLUSTRATIVE EXAMPLE 2

$C_1$ esterase inhibitor activity is found to be normal, excluding $C_1$ esterase inhibitor deficiency associated hereditary angioedema. However, DPP IV activity is found to be below the normal range. It is determined that it is not safe to restart the patient's ACE inhibitor, since the risk of angioedema is high.

OUTCOME B OF ILLUSTRATIVE EXAMPLE 2

The $C_1$ esterase inhibitor activity is found to be normal, excluding $C_1$ esterase inhibitor associated hereditary angioedema. The DPP IV activity is found to be below the normal range. The physician determines that treatment with the ACE inhibitor is still the best possible mode of treatment, once the angioedema is resolved, and the physician wants to determine if biomarkers and biochemical indicators (e.g., DPP IV activity) reveal that the angioedema was an isolated episode possibly related to some other exposure. Thus, the DPP IV activity is measured again in about 2 weeks or more after the first measurement (or after the angioedema has resolved).

OUTCOME B1 OF ILLUSTRATIVE EXAMPLE 2

The DPP IV activity found to remain depressed even after the angioedema has resolved. The physician determines that the risk of a recurrent episode of angioedema is high and orders that the ACE/vasopeptidase inhibitor treatment should not be restarted.

OUTCOME B2 OF ILLUSTRATIVE EXAMPLE 2

The DPP IV activity found to increase sufficiently after the angioedema has resolved or returns to normal, such that the physician determines that the angioedema was related to an isolated acquired influence. The physician determines that the patient's episode of angioedema is likely related to concurrent ciprofloxacin administration and that the risk of a recurrent episode of angioedema is low. The ACE or vasopeptidase inhibitor treatment is restarted at the original dose level or, alternatively, at a lower dose than the original dose of ACE or vasopeptidase inhibitor.

ILLUSTRATIVE EXAMPLE 3

A physician determines that a patient is in need of treatment with an ACE/vasopeptidase inhibitor. A blood sample is drawn from the patient and is processed to obtain a serum sample. The DPP IV and/or APP activity is determined for the individual. The patient is started on the inhibitor(s). The DPP IV and/or APP enzyme activity is checked periodically to determine the risk for angioedema and to determine if the risk is changing. The period between tests can be any period selected by the physician. In certain examples the period is about one week, in certain examples the period is about six months and in certain examples the period varies from test to test.

ILLUSTRATIVE EXAMPLE 4

Example 4 is the same as Example 3, except that the patient develops angioedema during the course of treatment with the inhibitor(s). Treatment with the inhibitor(s) is suspended until the angioedema is resolved and until the DPP IV and/or APP enzyme activity is found to be at a safe level(s) to resume treatment with the inhibitor(s).

LABORATORY EXAMPLES

The following Laboratory Examples have been included to illustrate preferred modes of the invention. Certain aspects of the following Laboratory Examples are described in terms of techniques and procedures found or contemplated by the present inventors to work well in the practice of the invention. These Laboratory Examples are exemplified through the use of standard laboratory practices of the inventors. In light of the present disclosure and the general level of skill in the art, those of skill will appreciate that the following Laboratory Examples are intended to be exemplary only and that numerous changes, modifications and alterations can be employed without departing from the spirit and scope of the invention.

LABORATORY EXAMPLE 1

Figure 5:
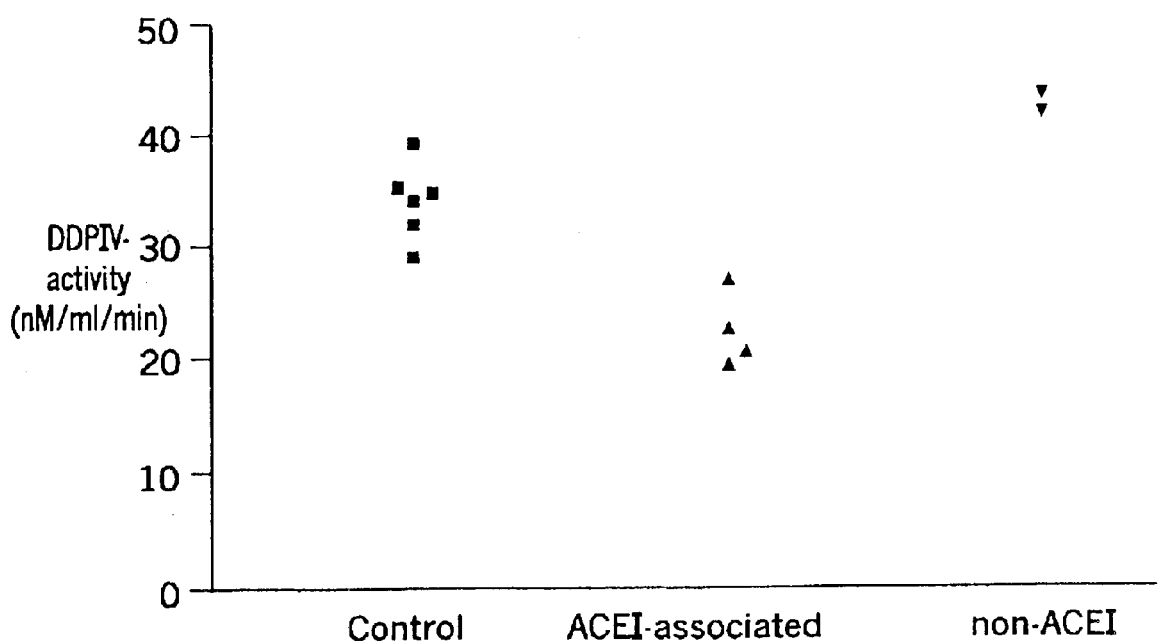
FIG. 5 is a plot depicting DDP IV activity (in nanomoles/milliliter/minute or nM/ml/min) in a control population (Control), a population with ACE inhibitor (ACEI) associated angioedema (ACEI-associated), and a population treated with an ACE inhibitor but without angioedema (non-ACEI).

One use of DPP IV enzyme activity as a biological marker is demonstrated in FIG. 5. In this example, DPP IV activity is in a range of about 28 to about 42 nM/ml/min in a control group. The control group comprises subjects that have received an ACE or vasopeptidase inhibitor and do not have angioedema (they are normotensive). Thus, 28 to 42 nM/ml/min is considered to be the normal range or control range for this particular population, in this example. DPP IV activity in a group of hypertensive subjects who have received an ACE inhibitor, but were free from angioedema, is in a range above the normotensive control group in this experiment. Thus, above 28 and preferably above 40 nM/ml/min is considered to be the normal range or control range for this particular group (for example, 40 to 50 nM/ml/min; for another example 40 to more than 40 nM/ml/min). A group receiving an ACE inhibitor and presenting with acute angioedema has reduced DPP IV enzymatic activity. The subject range is between 18 and 27 nM/ml/min, in this example. Thus, this group shows a reduction in the average and the median DPP IV activity compared to the hypertensive group. There is a significant difference in the ranges of DPP IV activity between these groups and the significance is greater than or equal to a 95% confidence interval.

Referring now to Table 5, Column A (NTN) is normotensive controls. Column B (HTN) is hypertensive controls (received ACE inhibitor at some time). Column C is a subject group with acute angioedema and receiving ACE inhibitor. Values that are outside a "range" can be outside of the 95% confidence interval, for example.

TABLE 5

RESULTS OF A CLINICAL TRIAL

| X Labels | A | B | C | D | E non- |
| X Labels | NTN | HTN | ACEI AE | ACEI AE | ACEI AE |
| --- | --- | --- | --- | --- | --- |
| X | Y | Y | Y | Y | Y |
| Number of values | 21 | 10 | 5 | 7 | 2 |
| Minimum | 24.80 | 28.08 | 23.97 | 19.68 | 41.25 |
| 25% Percentile | 34.21 | 30.28 | | 31.61 | |
| Median | 38.06 | 35.41 | 24.61 | 35.57 | 42.06 |
| 75% Percentile | 42.80 | 39.17 | | 43.15 | |
| Maximum | 51.59 | 39.75 | 28.38 | 43.57 | 42.87 |
| Mean | 37.76 | 34.59 | 25.32 | 35.12 | 42.06 |
| Std. Deviation | 6.300 | 4.243 | 1.774 | 8.511 | 1.146 |
| Std. Error | 1.375 | 1.342 | 0.7935 | 3.217 | 0.8100 |
| Lower 95% CI | 34.90 | 31.55 | 23.12 | 27.25 | 31.77 |
| Upper 95% CI | 40.63 | 37.62 | 27.53 | 42.99 | 52.35 |

References

The references listed below as well as all references cited in the specification are incorporated herein by reference to the extent that they supplement, explain, provide a background for or teach methodology, techniques and/or compositions employed herein. All cited patents and publications referred to in this application are herein expressly incorporated by reference. Also expressly incorporated herein by reference are the contents of all citations of GenBank accession numbers, LocusID, and other computer database listings.

Ariyoshi, (1993) *Trends Food Sci. Tech.*, May, 1993, p. 139
Baker (1991) *Cir. Shock* 33: 37–47
Barth et al., (1974) *Acta Biol. Med. Chem.* 32:157–174
Blais et al., (1999) *Immunopharmacology* 43: 293–302
Blais et al., (1999) *Peptides* 20: 421–430
Brown et al., (1996) *Clin. Pharmacol. Ther.* 60: 8–13
Damas et al., (1996) *N-S Arch. Pharmacol.* 354: 662–669
Dennes et al., (1992) *Brit. J. Pharmacol.* 105: 88; and Barnes et al., (1991) *FASEB J.*, 5: 678
Dzau, (1991) *New Engl. J. Med.* 324: 1124–1130
Emanueli et al., (1998) *Hypertension* 31:1299–1304
Ersahin et al., (1997) *J. Cardiovasc. Pharm.* 30: 96–101.
Fitzsimmons, (1980) *Rev. Physiol. Biochem. Pharmacol.* 87: 117
Fukasawa et al., (1981) *Biochim. Biophys. Acta* 657: 179–189
Fukusawa & Harada, (1981) *Arch. Biochem. Biophys.* 210: 230–237
Gainer et al., (1998) *New Engl. J. Med.* 339: 1285–92
Garrison et al., in *The Pharmacological Basis of Therapeutics*, 8th Edition, (Gilman, Goodman, Rall, Nies, and Taylor, eds), Pergamon Press, New York, 1990: p. 761–762
Hopsu-Havu & Glenner, (1966) *Histochem.* 7: 197–201
Jackson et al., (1988) *Nature* 335: 437
Kauffman et al., (1991) *Life Sci.* 49: 223–228
Kim et al., (2000) *J. Pharm. Exp. Ther.* 292: 295–298
Kitamura, (1995) *Br. J. Pharmacol.* 114: 6–7
Kohama et al., (1988) *Biochem. Biophys. Res. Comm.* 155 (1): 332
Maruyama et al., (1989) *Agric. Biol. Chem.* 53(10): 2763
Matsuda et al., (1992) *Nippon Nogeigaku Kaishi* 66(11): 1645
Matsumoto et al., (1994) *Nippon Shokuhin Kogyo Gakkaishi* 41(9): 589
Muramoto & Kawamora, (1991) *Food Ind.* 34(11): 18
Naftilan et al., (1989) *J. Clin. Invest.* 83: 1419
Nakamura et al., (1995) *J. Dairy Sci.* 78: 777
Orawski (1987) *Mol. Cell. Biochem.* 75: 123–132
Orawski et al., (1987) *Mol. Cell. Biochem.* 75: 123–132
Orawski et al., (1989) *Adv. Exp. Med. Biol.* 2478: 355–364
Oshima et al., (1979) *Biochim. Biophys. Acta* 556: 128
Oya et al., (1972) *Biochim. Biophys. Acta* 258: 591–599
Pasquero et al., (1992) *J. Hyperten.* 10: 1479–1484
Pesquero et al., (1992) *J. Hyperten.* 10: 1471–1478
Regoli et al., (1974) *Pharm. Rev.* 26: 69
Ryan et al., (1994) *J. Pharmacol. Exper. Thera.* 269: 941–947
Ryan, (1989) *Am. J. Physiol.* 257: L53–L60
Scharpe et al., (1990) *Clin. Chem.* 36: 984
Simmons & Orawski, (1992) *J. Biol. Chem.* 267, 4897–4903
Struyf et al., (1999) *J. Immunol.* 162: 4903–4909
Svensson et al., (1978) *Eur. J. Biochem.* 90: 489–498
Yoshimoto & Tsuru, (1982) *Biochem.* 91:1899–1906
Yoshimoto & Walter, (1977) *Biochim. Biophys. Acta*, 485: 391–401
Yoshimoto et al., (1978) *J. Biol. Chem.* 253: 3708–3716
Yoshimoto et al., (1994) *Arch. Biochem. Biophys.* 311: 28–34
European Patent No. EP174162
Japanese Patent No. 3-1671981
Japanese Patent No. 62-270533
Japanese Patent No. 64-5497
Japanese Patent No. 64-83096
U.S. Pat. No. 3,832,337
U.S. Pat. No. 4,191,753
U.S. Pat. No. 4,512,979
U.S. Pat. No. 4,585,758
U.S. Pat. No. 4,680,283
U.S. Pat. No. 4,692,459
U.S. Pat. No. 5,071,955
U.S. Pat. No. 5,449,661

It will be understood that various details of the invention may be changed without departing from the scope of the invention. Moreover, it is not the inventor's desire to be bound by theory or mechanism. Any theory or mechanism presented herein is included solely to supplement the disclosure, and should not be interpreted to impose any limitation on the claims presented hereinbelow. Therefore, the foregoing description is for the purpose of illustration only, and not for the purpose of limitation—the invention being defined by the claims.

What is claimed is:

1. A method of identifying a subject that is susceptible to developing an angioedemic condition during a course of treatment comprising administering one of an ACE inhibitor and a vasopeptidase inhibitor, comprising:
   (a) providing a biological sample from a subject;
   (b) determining an aminopeptidase P activity in the biological sample; and
   (c) comparing an aminopeptidase P activity in the biological sample to a standard aminopeptidase P activity, wherein a 10% or more reduction in the sample activity compared to the standard indicates that the subject is susceptible to developing an angioedema during a course of treatment comprising administering one of an ACE inhibitor and a vasopeptidase inhibitor.

2. The method of claim 1, wherein the vasopeptidase inhibitor comprises an angiotensin-converting enzyme inhibitor.

3. The method of claim 1, wherein the vasopeptidase inhibitor comprises a neutral endopeptidase inhibitor.

4. The method of claim 1, wherein the subject is a human.

5. The method of claim 1, wherein a 20% or more reduction in the aminopeptidase P activity in the biological sample, as compared to the standard aminopeptidase P activity indicates that the subject is susceptible to developing an angioedema during a course of treatment comprising administering one of an ACE inhibitor and a vasopeptidase inhibitor.

6. The method of claim 1, wherein a 30% or more reduction in the aminopeptidase P activity in the biological sample, as compared to the standard aminopeptidase P activity indicates that the subject is susceptible to developing an angioedema during a course of treatment comprising administering one of an ACE inhibitor and a vasopeptidase inhibitor.

7. A method of determining contraindication for administration of one of an ACE inhibitor and a vasopeptidase inhibitor, comprising:

(a) providing a biological sample obtained from a subject:

(b) determining an aminopeptidase P activity in the biological sample: and (c) comparing an aminopeptidase P activity in the biological sample to a standard aminopeptidase P activity range, wherein administration of the vasopeptidase inhibitor is contraindicated when the aminopeptidase P activity in the biological sample is outside the standard aminopeptidase P activity range.

8. The method of claim 7, wherein the vasopeptidase inhibitor comprises an angiotensin-converting enzyme inhibitor.

9. The method of claim 7, wherein the vasopeptidase inhibitor comprises a neutral endopeptidase inhibitor.

10. A method of screening an individual for compatibility with an administration of one of an ACE inhibitor and a vasopeptidase inhibitor, comprising:

(a) providing a biological sample obtained from a subject;

(b) determining a dipeptidyl peptidase IV activity in the biological sample; and (c) comparing a dipeptidyl peptidase IV activity in the biological sample to a standard dipeptidyl peptidase IV activity range, wherein administration of the vasopeptidase inhibitor is contraindicated when the dipeptidyl peptidase IV activity in the biological sample is below the standard dipeptidyl peptidase IV activity range, and wherein administration of the vasopeptidase inhibitor is indicated when the sample activity is either within or above the standard dipeptidyl peptidase IV activity range.

11. The method of claim 10, wherein the vasopeptidase inhibitor comprises an angiotensin-converting enzyme inhibitor.

12. The method of claim 10, wherein the vasopeptidase inhibitor comprises a neutral endopeptidase inhibitor.

13. A method of screening an individual for compatibility with an administration of one of an ACE inhibitor and a vasopeptidase inhibitor, comprising:

(a) providing a biological sample obtained from a subject;

(b) determining an aminopeptidase P activity in the biological sample; and (c) comparing an aminopeptidase P activity in the biological sample to a standard aminopeptidase P activity range, wherein administration of a vasopeptidase inhibitor is contraindicated when the sample activity is below the standard aminopeptidase P activity range, and wherein administration of the vasopeptidase inhibitor is indicated when the sample activity is either equal to or above the standard aminopeptidase P activity range.

14. The method of claim 13, wherein the vasopeptidase inhibitor comprises an angiotensin-converting enzyme inhibitor.

15. The method of claim 13, wherein the vasopeptidase inhibitor comprises a neutral endopeptidase inhibitor.

16. The method of claim 10, wherein the dipeptidyl peptidase IV activity in the biological sample is below the standard dipeptidyl peptidase IC activity range by a significant difference at a level of significance of greater than or equal to a 95% confidence interval.

* * * * *